(12) United States Patent
Gandel

(10) Patent No.: US 11,395,925 B2
(45) Date of Patent: Jul. 26, 2022

(54) DEVICE AND METHOD FOR INDUCING LYPOLYSIS IN HUMANS

(71) Applicant: Brian A. Gandel, Boca Raton, FL (US)

(72) Inventor: Brian A. Gandel, Boca Raton, FL (US)

( * ) Notice: Subject to any disclaimer, the term of this patent is extended or adjusted under 35 U.S.C. 154(b) by 179 days.

(21) Appl. No.: 16/397,098

(22) Filed: Apr. 29, 2019

(65) Prior Publication Data

US 2019/0329065 A1   Oct. 31, 2019

Related U.S. Application Data

(60) Provisional application No. 62/664,221, filed on Apr. 29, 2018.

(51) Int. Cl.
| | |
|---|---|
| *A61N 5/06* | (2006.01) |
| *A61B 18/20* | (2006.01) |
| *A61N 7/02* | (2006.01) |
| *A61B 18/00* | (2006.01) |

(52) U.S. Cl.
CPC .......... *A61N 5/0616* (2013.01); *A61B 18/203* (2013.01); *A61B 2018/00464* (2013.01); *A61N 5/062* (2013.01); *A61N 7/02* (2013.01); *A61N 2005/0658* (2013.01)

(58) Field of Classification Search
CPC ........ A61N 5/0616; A61N 5/062; A61N 7/02; A61N 2005/0658; A61B 18/203; A61B 2018/00464
USPC .......................................................... 607/88
See application file for complete search history.

(56) References Cited

U.S. PATENT DOCUMENTS

| | | | |
|---|---|---|---|
| 6,443,978 B1 * | 9/2002 | Zharov ................ | A61N 5/0616 606/2 |
| 8,813,756 B1 | 8/2014 | Shanks et al. | |
| 10,046,172 B2 | 8/2018 | Butters et al. | |
| 2004/0210214 A1 * | 10/2004 | Knowlton ............ | A61B 18/203 606/41 |
| 2004/0232359 A1 * | 11/2004 | Fiset .................... | A61N 5/0614 250/504 R |
| 2007/0282318 A1 * | 12/2007 | Spooner ............. | A61B 18/1206 607/101 |

(Continued)

FOREIGN PATENT DOCUMENTS

| | | |
|---|---|---|
| KR | 101562637 | 10/2015 |
| KR | 20170119292 | 10/2017 |

OTHER PUBLICATIONS

Cohen, M., et al., "CORE™ Technology: Understanding Penetration Depths of Different RF Modes." (2009), pp. 1-2.

(Continued)

*Primary Examiner* — Carl H Layno
*Assistant Examiner* — Michael J Lau
(74) *Attorney, Agent, or Firm* — The Concept Law Group, PA; Scott D. Smiley; Scott M. Garrett

(57) ABSTRACT

A device includes light sources, electromagnetic field generators, and vibration components to apply a variety of treatment regimens to a living animal organism, including a human person or a body part of a person. The light and electromagnetic therapy are applied at frequencies which have physiological effects, and which can be combined to induce lipolysis, stimulate muscle, and achieve other effects. Feedback is used to dynamically adjust the intensity, duration, and other parameters of the light, electromagnetic, and vibration treatment modalities.

20 Claims, 16 Drawing Sheets

(56) References Cited

U.S. PATENT DOCUMENTS

| | | | |
|---|---|---|---|
| 2008/0312647 A1* | 12/2008 | Knopp | A61B 18/1477 |
| | | | 606/41 |
| 2010/0016651 A1* | 1/2010 | Sivo | A61N 1/40 |
| | | | 600/14 |
| 2012/0078328 A1* | 3/2012 | Vancraeyenest | A61N 5/0613 |
| | | | 607/88 |
| 2015/0342824 A1* | 12/2015 | Simonson | A61N 5/0613 |
| | | | 601/18 |
| 2016/0066994 A1 | 3/2016 | Shanks | |
| 2016/0184568 A1* | 6/2016 | Harris | A61N 1/0492 |
| | | | 604/20 |
| 2016/0228324 A1* | 8/2016 | Garteiser | A61H 23/04 |
| 2016/0317827 A1* | 11/2016 | Schwarz | A61N 2/002 |
| 2017/0007309 A1* | 1/2017 | DeBenedictis | A61K 31/047 |
| 2017/0106201 A1* | 4/2017 | Schwarz | A61N 5/0625 |
| 2017/0333705 A1* | 11/2017 | Schwarz | A61N 1/40 |
| 2018/0085023 A1* | 3/2018 | Tillander | G01R 33/4804 |
| 2018/0103991 A1* | 4/2018 | Linhart | A61B 18/1477 |
| 2019/0175144 A1* | 6/2019 | O'Brien | A61N 7/00 |
| 2019/0192873 A1* | 6/2019 | Schwarz | A61F 7/00 |
| 2020/0069458 A1* | 3/2020 | Pham | A61F 7/0085 |

OTHER PUBLICATIONS

Adatto, M., et al., "Reduction in adipose tissue volume using a new high-power radiofrequency technology combined with infrared light and mechanical manipulation for body contouring." Lasers in medical science 29.5 (2014): pp. 1627-1631.

Sadick, N., "Treatment for cellulite." International journal of women's dermatology 5.1 (2019): pp. 68-72.

Emsculpt, Emsculpt Technology for Non-Thermal Induction of Muscle Growth and Fat Apoptosis, Mechanism of Action, downloaded from https://hayesvalleymed.com/pdfs/Emsculpt_CLIN_Mechanism-of-action-paper_ENUS100.pdf, on Feb. 10, 2021, pp. 1-2.

Modern Aesthetics, "Paradigm Shift: The Science Behind Emsculpt's HIFEM Technology for Reducing Fat and Building Muscle", Insert to Modern Aesthetics, Jul.-Aug. 2018, pp. 20-21.

Weiss, R.,M.D.,et al., Histological in Vivo Study: the Mechanism of Action: "Induction of Fat Apoptis by a Non-Thermal Device: Safety and Mechanism of Action of Non-Invasive HIFEM Technology Evaluated in a Histological Porcine Model", Presented at the Annual Meeting of the American Society for Laser Medicine and Surgery in 2018, downloaded from https://www.renewmedispa.com/wp-content/uploads/2019/03/Emsculpt_CLIN_Study-1_ENUS100.pdf, on Feb. 11, 2021, pp. 1-2.

Katz M.D., et al., "Ultrsonography Study: Subcutaneous Fat Reduction: Changes in Subcutaneous Abdominal Fat Thickness Following High-Intensity Focused Electro-Magnetic (HIFEM®) Field Treatments: A Multi Center Ultrasound Study.", Presented at the Annual Meeting of the American Society for Laser Medicine and Surgery, 2018 Dallas, TX, pp. 1-2.

Kent M.D., et al., "Computed Tomography Study: Simultaneous Fat and Muscle Effect-Computed Tomography (CT) Based Evidence of Simultaneouschanges in Human Adipose and Muscle Tissues Following a High Intensity Focused Elelctro-Magnetic Field (HIFEM®) Application: A New Method for Non-Invasive Body Sculpting.", Presented at the Annual Meeting of the American Society for Laser Medicine and Surgery, 2018 Dallas, TX, pp. 1-2.

Jacob M.D, et al., Waist Circumference Reduction Testedin a Multicentric Study—A Novel Non-Invasive Technology Based on Simultaneous Induction of Changes in Adipose and Muscle Tissues: Safetyand Efficacy of a High Intensity Focused Electro-Magnetic Field Device Used for Abdominal Body Shaping, Presented at the Annual Meeting of the American Society for Laser Medicine and Surgery, 2018 Dallas, TX. pp. 1-2.

Busso, M.D., et al., "An Initial Study Investigated the Effects on Buttocks—Efficacy of High Intensity Focused Electro-Magnetic Field Therapy When Used for Non-Invasive Buttocks Augmentation and Lifting: A Clinical Study.", Presented at the Annual Meeting of the American Society for Laser Medicine and Surgery, 2018 Dallas, TX., pp. 1-2.

Jacob M.D, et al.,"A Large-Scale Multicentric Study: Non-Invasive Butt Lifting Effects—High Intensity Focused Electro-Magnetic Technology (HIFEM) for Non-Invasive Buttocks Lifting and Toning of Gluteal Muscles: A Multi-Center Efficacy and Safety Study.", 2018, p. 1.

Ward Photonics, LLC, "A Retrospective Analysis of the Effects of Red Light Therapy on Body Contouring", Mar. 9, 2016, pp. 1-16.

Ward Photonics, LLC, "Intra-Surgical Study of Fat Reduction In Vivo", Mar. 1, 2017, p. 1.

Roche M.D., et al., "Low-Level Laser Therapy for Reducing the Hip,Waist, and Upper Abdomen Circumference of Individuals with Obesity", Photomedicine and Laser Surgery, vol. 35, No. 3, Published online on Dec. 9, 2016, pp. 142-149.

Ibrahim, Mohab M., et al. "Long-lasting antinociceptive effects of green light in acute and chronic pain in rats." Pain vol. 158, No. 2 (2017): pp. 347-360.

Park, Phil June, Jae Youl Cho, and Eun-Gyung Cho. "Specific visible radiation facilitates lipolysis in mature 3T3-L1 adipocytes via rhodopsin-dependent β3-adrenergic signaling." European journal of cell biology 96.4 (2017): pp. 301-311.

Kim, Eun Ju, et al. "UV modulation of subcutaneous fat metabolism." Journal of investigative dermatology 131.8 (2011): 1720-1726.

Miranda, PhD, et al.,"Using pre-exercise photobiomodulation therapy combining super-pulsed lasers and light-emitting diodes to improve performance in progressive cardiopulmonary exercise tests." Journal of Athletic Training 51.2 (2016): pp. 129-135.

Albuquerque-Pontes, Gianna Móes, et al. "Effect of pre-irradiation with different doses, wavelengths, and application intervals of low-level laser therapy on cytochrome c oxidase activity in intact skeletal muscle of rats." Lasers in medical science 30.1 (2015): pp. 59-66.

Kono, K., M.D., "Comparison study of intense pulsed light versus a long-pulse pulsed dye laser in the treatment of facial skin rejuvenation." Annals of plastic surgery 59.5 (Nov. 2007): pp. 479-483.

Montazeri, Katayoon, Soheila Mokmeli, and Maryam Barat. "The Effect of Combination of Red, Infrared and Blue Wavelengths of Low-Level Laser on Reduction of Abdominal Girth: A Before-After Case Series." Journal of lasers in medical sciences 8.Suppl 1 (2017): pp. S22-S26.

Hashmi, Javad T., et al. "Effect of pulsing in low-level light therapy." Lasers in surgery and medicine 42.6 (Aug. 2010): pp. 450-466.

Sommer, Andrei P., and Dan Zhu. "Facial Rejuvenation in the Triangle of ROS." Crystal growth & design 9.10 (2009) pp. 4250-4254.

Norman Christel, et al. "Salicylic acid is an uncoupler and inhibitor of mitochondrial electron transport." Plant physiology 134.1 (2004): pp. 492-501.

Rena, Graham, and Kei Sakamoto. "Salicylic acid: old and new implications for the treatment of type 2 diabetes?." Diabetology international 5.4 (2014) pp. 212-218.

Gammone, Maria Alessandra, and Nicolantonio D'Orazio. "Anti-obesity activity of the marine carotenoid fucoxanthin." Marine drugs 13.4 (2015): pp. 2196-2214.

Lou, P., et al., "Mitochondrial uncouplers with an extraordinary dynamic range." Biochemical Journal 407.1 (2007) pp. 129-140.

Komlodi, T., et al. "Methylene blue stimulates substrate-level phosphorylation catalysed by succinyl-CoA ligase in the citric acid cycle." Neuropharmacology 123 (2017): pp. 287-298.

Gibellini, L., et al.,"Natural compounds modulating mitochondrial functions." Evidence-Based Complementary and Alternative Medicine 2015 (2015), pp. 1-13.

Mukherjee, P., et al.,"Bioactive compounds from natural resources against skin aging." Phytomedicine 19.1 (2011): 64-73.

Nusgens, B., et al., "Topically applied vitamin C enhances the mRNA level of collagens I and III, their processing enzymes and

(56) References Cited

OTHER PUBLICATIONS tissue inhibitor of matrix metalloproteinase 1 in the human dermis." Journal of Investigative Dermatology 116.6 (Jun. 2001): pp. 853-859.
Armanini, D., et al., "Glycyrrhetinic acid, the active principle of licorice, can reduce the thickness of subcutaneous thigh fat through topical application." Steroids 70.8 (2005): pp. 538-542.
Kong, S. et al., "The protective effect of 18β-Glycyrrhetinic acid against UV irradiation induced photoaging in mice." Experimental gerontology 61 (2015): pp. 147-155.
Dupont, E. et al., "An integral topical gel for cellulite reduction: results from a double-blind, randomized, placebo-controlled evaluation of efficacy." Clinical, cosmetic and investigational dermatology 7 (Feb. 20, 2014) pp. 73-88.
Roure, R., et al., "Evaluation of the efficacy of a topical cosmetic slimming product combining tetrahydroxypropyl ethylenediamine, caffeine, carnitine, forskolin and retinol, in vitro, ex vivo and in vivo studies." International journal of cosmetic science 33.6 (2011): pp. 519-526.
Bissett, D.L., et al., "Topical niacinamide reduces yellowing, wrinkling, red blotchiness, and hyperpigmented spots in aging facial skin 1." International journal of cosmetic science 26.5 (2004): pp. 231-238.
Song, N., et al.,"Induction of thermogenic adipocytes: molecular targets and thermogenic small molecules." Experimental & molecular medicine 49.7 (2017): pp. 1-11.
Ito, M., et al., "Capsaicin mimics mechanical load-induced intracellular signaling events: involvement of TRPV1-mediated calcium signaling in induction of skeletal muscle hypertrophy." Channels 7.3 (2013): pp. 221-224.
Bertin, C., et al., "Clinical evidence for the activity of tetrahydroxypropyl ethylenediamine (THPE), a new anti-aging active cosmetic." Journal of drugs in dermatology: Journal of Drugs in Dermatology, vol. 10, Issue 10 (Oct. 2011): pp. 1102-1105.
Vegas, J., et al., "Focal Coil Design for Transcranial Magnetic Stimulation on Mice.", Bachelor Graduation Thesis TUDelft—Electric Engineering, Jul. 8, 2016, pp. 1-69.
Chila, A., Executive Editor, et al., Published in Partnership with American Osteopathic Medicine, "Chapter 16: Chronic Pain Management", Foundations of Osteopathic Medicine, 3rd Edition, 2011, pp. 1-50.
Noites, et al. "Effects of aerobic exercise associated with abdominal microcurrent: a preliminary study." The Journal of Alternative and Complementary Medicine 21.4 (2015): p. 1.
Liboff, A., "Chapter 34: Electromagnetic Therapy", In book: Bioelectromagnetic and Subtle Energy Medicine A PrimerPublisher: CVCEditors: Paul J Rosch, (pp. 375-388).
Oliveira, P., et al., "Training effects of alternated and pulsed currents on the quadriceps muscles of athletes." International journal of sports medicine 39.07 (2018): pp. 535-540.
Ke, Yin-Lung, et al. "Influence of electromagnetic signal of antibiotics excited by low-frequency pulsed electromagnetic fields on growth of *Escherichia coli*." Cell biochemistry and biophysics 67.3 (2013): pp. 2-8.
Dover, Jeffrey S., et al., "Results of a Survey of 5,700 Patient Monopolar Radiofrequency Facial Skin Tightening Treatments: Assessment of a Low-Energy Multiple-Pass Technique Leading to a Clinical End Point Algorithm", Dermatologic Surgery, Aug. 2007, vol. 33, Issue 9, pp. 900-907.
McRae, Elizabeth, et al., "Independent Evaluation of Low-Level Laser Therapy at 635 nm for Non-Invasive Body Contouring of the Waist, Hips, and Thighs", Lasers in Surgery and Medicine, 2013, vol. 45, pp. 1-7.
Nestor, Mark, et al., "Effect of 635nm Low-level Laser Therapy on Upper Arm Circumference Reduction", The Journal of Clinical and Aesthetic Dermatology, Feb. 2012, vol. 5, No. 2, pp. 42-48.
Jackson, Robert, et al., "A Double-Blind,Placebo-Controlled Randomized Trial Evaluating the Ability of Low-Level Laser Therapy to Improve the Appearance of Cellulite", Lasers in Surgery and Medicine, 2013, vol. 145, pp. 141-147.

Morabito, Caterina, et al., "Extremely Low-Frequency Electromagnetic Fields Affect Myogenic Processes in C2C12 Myoblasts: Role of Gap-Junction-Mediated Intercellular Communication", BioMed Research International, Published May 21, 2017, pp. 1-10.
Saggini, Raoul, et al., "Vibration in Neurorehabilitation: a narrative review", Medical Research Archives, Nov. 2017, vol. 5, Issue 11, pp. 1-10.
Choi, Min Sik et al., "Amber Light (590 nm) Induces the Breakdown of Lipid Droplets through Autophagy-Related Lysosomal Degradation in Differentiated Adipocytes", Scientific Reports, Published Jun. 27, 2016, pp. 1-11.
Gu, Guanbao, et al., "Stimulation of TRPV1 by Green Laser Light", Evidence-Based Complementary and Alternative Medicine, vol. 2012, Article ID 857123, 2012, pp. 1-8.
Purnell, Marcy C., et al., "Bio-field array: a dielectrophoretic electromagnetic toroidal excitation to restore and maintain the golden ratio in human erythrocytes", Physiological Reports, 2018, vol. 6, Issue 1, pp. 1-16.
Ondrusova, Katarina, et al., "Subcutaneous white adipocytes express a light sensitive signaling pathway mediated via a melanopsin/TRPC channel axis", Scientific Reports, Published online Nov. 27, 2017, vol. 7, No. 16332, pp. 1-9.
Kim, Hong Bae, et al., "Pulse frequency dependency of photobiomodulation on the bioenergetic functions of human dental pulp stem cells", Scientific Reports, Published online Nov. 21, 2017, vol. 7, No. 15927, pp. 1-12.
Blank, Martin, et al., "Optimal frequencies for magnetic acceleration of cytochrome oxidase and Na,K-ATPase reactions", Bioelectrochemistry, 2001, vol. 53, pp. 171-174.
Shackell, Erin M., et al., "Mind Over Matter: Mental Training Increases Physical Strength", North American Journal of Psychology, 2007, vol. 9, No. 1, pp. 1-13.
Gavenis et al., "Millicurrent stimulation of human articular chondrocytes cultivated in a collagen type-I gel and of human osteochondral explants", BMC Complementary & Alternative Medicine, 2010, vol. 10, Issue 43, pp. 1-9.
Aurelio, Marco, et al., "Low-Frequency Pulsed Current Versus Kilohertz-Frequency Alternating Current: A Scoping Literature Review", 2018, Archives of Physical Medicine and Rehabilitation, vol. 99, pp. 792-805.
Gabay, Ilan, et al., "Increasing the penetration depth for ultrafast laser tissue ablation using glycerol based optical clearing", downloaded from https://www.spiedigitallibrary.org on Apr. 16, 2019, pp. 1-8.
Nagarkatti, Prakash, et al., "Cannabinoids as novel anti-inflammatory drugs", Future Medical Chemistry, 2009, vol. 1, No. 7, pp. 1-25.
Hasan, Mahmudul, et al., "Designing a Transcranial Magnetic Stimulator Coil for Deep Brain Stimulation", Proceedings of the 9th International Conference on Electrical and Computer Engineering, Dec. 7-11, 2016, pp. 1-5.
Deng, Zhi-De, et al., "Electric field depth-focality tradeoff in transcranial magnetic stimulation: Simulation comparison of 50 coil designs", Brain Stimulation 6, No. 1, 2013, pp. 1-27.
Jiang, Yuxiang, et al., "Development of a Unipolar Pulse Electromagnetic Field Apparatus for Magnetic Therapy", IEEE Instrumentation & Measurement Magazine, Oct. 2018, vol. 21, No. 5, pp. 1-8.
Esmat, Samia M., et al., "Low Level Light-Minoxidil 5% Combination Versus Either Therapeutic Modality Alone in Management of Female Patterned Hair Loss: A Randomized Controlled Study", Lasers in Surgery and Medicine, 2017, vol. 49, No. 9, pp. 1-9.
Fodor, L., et al., "Chapter 2: Light Tissue Interactions", Aesthetic Applications of Intense Pulsed Light, 2011, pp. 11-20, Published by Springer, ISBN: 978-1-84996-455-5.
Funk, Richard, "Coupling of pulsed electromagnetic fields (PEMF) therapy to molecular grounds of the cell", American Journal of Translational Research, Published May 2018, vol. 10. No. 5., pp. 1260-1272.
Kinney, Brian, et al., "High Intensity Focused Electromagnetic Therapy Evaluated by Magnetic Resonance Imaging: Safety and Efficacy Study of a Dual Tissue Effect Based Non-Invasive Abdominal Body Shaping", Lasers in Surgery and Medicine, 2019, vol. 21, pp. 40-46.

(56) References Cited

OTHER PUBLICATIONS

Hamad, Farhad, et al., "Influences of different low level laser power at wavelength 635 nm for two types of skin; dark and light", Proceedings of the 7th IMT-GT UNINET and the 3rd International PSU-UNS Conferences on Bioscience, Oct. 7-8, 2010, pp. 1-7.
Ke, Yin-Lung, et al., "Influence of Electromagnetic Signal of Antibiotics Excited by Low-Frequency Pulsed Electromagnetic Fields on Growth of Escherichia coli", Cell biochemistry and biophysics, Dec. 2013, vol. 67, No. 3, pp. 1229-1237.
Bellew, James W., et al., "Efficiency of neuromuscular electrical stimulation: A comparison of elicited force and subject tolerance using three electrical waveforms", Physiotherapy Theory and Practice, 2018, vol. 34, No. 7, pp. 1-8.
Cosic, et al., "Environmental Light and Its Relationship with Electromagnetic Resonances of Biomolecular Interactions, as Predicted by the Resonant Recognition Model", International Journal of Environmental Research and Public Health, Published Jun. 29, 2016, pp. 1-10.
Ashida, Yuki, et al., "Effects of contraction mode and stimulation frequency on electrical stimulation-induced skeletal muscle hypertrophy", Journal of Applied Physiology, Oct. 26, 2017, vol. 124, No. 2, pp. 341-348.
Makarov, S. et al., "Design and Analysis of a Whole Body Non-Contact Electromagnetic Stimulation Device with Field Modulation", bioRxiv preprint first posted online Sep. 13, 2018; doi: http://dx.doi.org/10.1101/416065, pp. 1-29.
Tiittanen, Ville-Valtteri, "Magnetic stimulation using moving permanent magnets", Thesis submitted for examination for the degree of Master of Science in Technology, Aalto University School of Science, Espoo, Finland, Apr. 17, 2015, pp. 1-53.
Khdour, Omar M., et al., "Lipophilic methylene blue analogues enhance mitochondrial function and increase frataxin levels in a cellular model of Friedreich's ataxia", Bioorganic & Medicinal Chemistry, 2018, vol. 26, pp. 3359-3369.
Carelli, Stephana, et al., "Mechanical Activation of Adipose Tissue and Derived Mesenchymal Stem Cells: Novel Anti-Inflammatory Properties", International Journal of Molecular Sciences, published Jan. 16, 2018, vol. 219, No. 1., pp. 1-16.
Vajrala, Vijayanand, et al., "Effects of Oscillatory Electric Fields on Internal Membranes: An Analytical Model", Biophysical Journal, Mar. 2008, vol. 94, No. 6, pp. 2043-2052.
Al-Mutawaly, Nafia, "Neuro Magnetic Stimulation: Engineering Aspects", Thesis submitted to the School of Graduate Studies in Partial Fulfillment of the Requirements for the Degree of Doctor of Philosophy, McMaster University, Dec. 2012, pp. 1-194.
Verginadis, I., et al., "Analgesic effect of the electromagnetic resonant frequencies derived from the NMR spectrim of morphine", Electromagnetic Biology and Medicine, 2012, pp. 1-10.
Redustim, "Medical Devices for the Reduction of Health Risks Related to Excess of Abdominal Fat", www.redustim.com., pp. 1-12.
Beilin, G., et al., "Impact of electromagnetic fields stimulation on metabolic syndrome, infertility and abdominal fat-related diseases for overweight or obese patients", Published Aug. 30, 2018 in Integrative Obesity Diabetes, vol. 3, No. 3, pp. 1-6.
Stiff, Mel C., et al., "Scientific Data on Electrostimulation", pp. 1-19.
Park, Gi, et al., Low-intensity microcurrent therapy promotes regeneration of atrophied calf muscles in immobilized rabbits, The Journal of Biomedical Research, 2019, vol. 33, No. 1, pp. 1-8.
Cheon, Songhee, et al. "Pulsed Electromagnetic Field Elicits Muscle Recovery via Increase of HSP 70 Expression after Crush Injury of Rat Skeletal Muscle", Journal of Physical Therapy Science, 2012, vol. 24, No. 7, pp. 589-592.
Brushart, Thomas M., et al., "Electrical Stimulation Promotes Motoneuron Regeneration without Increasing Its Speed or Conditioning the Neuron", The Journal of Neuroscience, Aug. 1, 2002, vol. 22, No. 15, pp. 6631-6638.
Bragin, Denis E., et al., "Increases in microvascular perfusion and tissue oxygenation via pulsed electromagnetic fields in the healthy rat brain", Journal of Neurosurgery, 2014, pp. 1-9.
Xu, Haixia et al., "Low frequency pulsed electromagnetic field promotes C2C12 myoblasts proliferation via activation of MAPK/ERK pathway", Biochemical and Biophysical Research Communications, 2016, vol. 479, No. 1, pp. 97-102.
Downie, Jeanine et al., Contactless Abdominal Fat Reduction with Selective RF Evaluated by Magnetic Resonance Imaging (MRI): Case Study, Journal of Drugs in Dermatology, Apr. 2016, vol. 15, Issue 4, pp. 491-495.
McDaniel, David, et al., Evaluation of the Safety and Efficacy of a Non-contact Radiofrequency Device for the Improvement in Contour and Circumferential Reduction of the Inner and Outer Thigh, Journal of Drugs in Dermatology, Dec. 2015, vol. 14, Issue 12, pp. 1422-1424.
Fritz, Klaus, et al., Long-term follow-up on patients treated for abdominal fat using a selective contactless radio frequency device, Journal of Cosmetic Dermatology, Accepted Aug. 28, 2017, pp. 1-5.
Pumprla, J., et al., "Non-contact radiofrequency-induced reduction of subcutaneous abdominal fat correlates with initial cardiovascular autonomic balance and fat tissue hormones: safety analysis", F1000 Research, Feb. 20, 2015, vol. 4, No. 49, pp. 1-10.
McDaniel, D., et al. "Human Adipocyte Apoptosis Immediately Following High Frequency Focused Field Radio Frequency", Journal of Drugs in Dermatology, vol. 14, Jun. 2015, Issue 6, pp. 622-623.
Hayre, N., et al., "A Clinical Evaluation of a Next Generation, Non-Invasive, elective Radiofrequency, Hands-Free, Body-Shaping Device", Journal of Drugs in Dermatology, vol. 15, Issue 12, Dec. 2016, pp. 1557-1561.
European Patent Office, Extended European Search Report for Application No. 19796567.6, dated Dec. 2, 2021, pp. 1-5.

\* cited by examiner

DEVICE AND METHOD FOR INDUCING LYPOLYSIS IN HUMANS

CROSS-REFERENCE TO RELATED APPLICATION

This application claims priority to U.S. Provisional Patent Application No. 62/664,221, filed 29 Apr. 2018, the entirety of which is incorporated by reference.

FIELD OF THE DISCLOSURE

The present disclosure relates to deices and apparatuses that induce weight loss in humans through lipolysis, and more particularly to an apparatus and method for inducing body fat loss utilizing optical emitters, electromagnetic coils, mechanical vibration, and topical creams in a holistic combination.

BACKGROUND

Many consumers dissatisfied with results from diet, exercise, and pharmaceutical intervention resort to surgical procedures, such as liposuction, to achieve a rapid reduction in bodyfat. Although surgical methods can achieve quick results, the removal of localized adipose tissue often results in dysmorphic fat accumulation if the patient regains weight in the future. Surgery is both painful and invasive, and risks include bruising, infection, and tissue trauma. Even when performed properly, liposuction can damage surrounding tissues.

A number of less invasive destructive fat loss techniques have been developed. Utilizing cryolipolysis, ultrasound, and/or radio frequencies, the techniques kill localized adipocytes, which are metabolized and excreted by the body. Although less invasive than surgery, these approaches often cause trauma to surrounding tissues, and can result in future dysmorphic fat accumulation. The results are not immediate, taking 3-4 months to see the full effect.

There have also been recent developments in non-invasive procedures utilizing laser and LED radiation to reduce adipocyte volume. Laser frequencies of 633 nm, 670 nm, and 820 nm have been employed. During treatment, cytochrome c oxidase in the mitochondria becomes oxidized indicating increased aerobic respiration and lipid metabolism. Cytochrome c oxidase is the chromophore excited by the irradiation, modulating its redox state and enhancing metabolism in the cell.

There are, however, dangers associated with laser-induced lipolysis: because lasers emit a focused beam of coherent light, the power of lasers must be kept low in order to avoid tissue damage. Also, laser-based products are capable of causing irreversible eye damage since they are capable of concentrating a powerful tightly-focused beam of light on the retina (up to 60,000 Watts/cm$^2$).

Because of the risks of high power lasers and their limited wavelengths, non-invasive procedures using LED light have been developed. As with laser-induced lipolysis, cytochrome c oxidase is the chromophore excited by the irradiation, modulating its redox state and enhancing metabolism in the adipocyte. For example, Lipo-Light, produced by Innovate Photonics Ltd is one such commercially available product. It employs six paddles each containing 25 LEDs, and produces 2.4 watts total from all 6 paddles. Each paddle must be strapped directly to the patient's skin for at least 20 minutes during treatments. The medical practitioner is unable to view directly the interaction of the paddles with the skin, and application of the discrete paddles results in gaps between the paddles not exposed to the LED light.

Another device, UltraSlim™, produced by Ward Photonics LLC, uses a single array of LED emitters to induce lipolysis (U.S. Pat. No. 9,498,641 B2). The LEDs emit 635 nm red light, and a total of about 40,000 Lux. The device reduces the lipid content of subcutaneous adipocytes in the target area in 8 minutes. To tighten facial skin, 20 minutes is required.

Only a limited portion of the body can be treated at one time, however. To treat the entire body (not including the face), the device must be repositioned 5-6 times with the LED array approximately 1-8 inches from the patient. The irradiation coverage is highly operator dependent since the operator must reposition the unit without any precise measurement, and the distance between the optical emitter and patient needs to be adjusted each time the unit is repositioned. Treatment time for the body and the chest is 48 minutes. To treat the face, another 20 minutes is required, for a total treatment time of 68 minutes (not including the time necessary to reposition the unit).

Additionally, the machine employs a monochromatic array of 635 nm LEDs, therefore the light irradiation only penetrates several cm into the body, limiting the number of adipocytes targeted during each treatment. The system does not directly address cellulite, nor does it assist in the elimination of the waste products from lipolysis that the body clears through the lymphatic system. Finally, the device does not attempt to optimize light penetration which attenuates with increasing adipose tissue depth, address the cell's tendency to stop responding or become resistant to one peak illumination frequency, or optimize the increased biochemical reactions in the mitochondria resulting from photo stimulation of cytochrome c.

The owner of Ward Photonics LLC, (renamed Blue Water Innovations, LLC in 2016) has submitted a patent for an updated version of UltraSlim™ named UltraSmooth™ which claims to address cellulite (US 2015/0127075A1). This replaces the red 635 nm diodes with green 529.6 nm diodes. Green light, it has been found, works better than red light for treating cellulite, and has been approved by the FDA for decreasing the appearance of cellulite. Green light has also been found to even out skin tone, and since it does not penetrate as deep as red light, may be better at skin tightening. The major chromatophore of 529.6 nm light is a cell surface receptor rather than cytochrome c, however, the end result is still stimulation of mitochondrial activity in adipocytes. The Ward Photonics device delivers 8.8 Joules of energy to subcutaneous adipocytes, requiring up to 25 min (the previous generation delivered 2.88 Joules, requiring up to 8 min.). Note that in 25 min, the previous generation device would deliver 9 Joules. The irradiance of the new Ward Photonics device is several mW/cm$^2$ less than the original versions, explaining the difference in energy output. Like the previous generation Ward Photonics device, this machine is still incapable of treating the entire body at one time. It does not address lymphatic drainage, and uses only one peak frequency of light.

Redustim™ (U.S. Pat. No. 9,403,028), by Cosmosoft, is a device that uses a 50 Hz pulsed electromagnetic field with a strength of 2 gauss. It stimulates passive contraction of smooth and striated muscle via induction of calcium release from the sarcoplasmic reticulum, which burns calories. The muscle contractions are not felt, and the procedure is reported to be painless. The device requires pads to be strapped to the arms, legs, abdomen, and face. The device is capable of burning both visceral and subcutaneous fat, reducing cellulite, and tightening the skin. An estimated 800 calories of both visceral and subcutaneous fat is lost per 30 min session. A disadvantage of the device is that it requires pads to be placed on the body, and it uses uncomfortable inflatable pressure cuffs within the pads to promote lymphatic drainage. The results are far more modest than LED based therapies like UltraSlim™. The device is also not available in the United States.

Low intensity pulsed electromagnetic fields (PEMF) can also accelerate weight loss. On the biophysical level, as PEMF therapy increases the circulation of electrons across the cell membrane, a parallel phenomenon seems to occur: the acceleration of ATP synthesis and of other aspects of the cell's biochemical anabolism. As electrons are drawn to the inner membrane, they increase the ionic charge inside the cell and increase the total membrane potential, which in turn stimulates the activity of the Na+/K+ pump in the cell membrane and ATP production. The Na+/K+ pump transfers 3Na+ out of the cell for every 2K+ it brings into the cell. Since water follows sodium, any edema in the cell is relieved. Electrons are also absorbed by the cytochromes within mitochondria, increasing cellular respiration and metabolism. PEMF therapy mechanically stimulates blood vessels and blood flow, as well as mechanically stimulating the lymphatic vessels helping eliminate waste products and toxins from the body. PEMF therapy on its own appears to have a modest effect on weight loss, however, there are no clinical studies demonstrating the magnitude of the effect. It does, however, optimize metabolism and lymphatic drainage. Increasing cellular metabolism and elimination of waste products, as well the anti-oxidant effect of absorbed electrons, should be synergistic with light therapy: the accumulation of reactive oxygen species (ROS) generated by lipid metabolism, as well as the buildup of fatty acid chains and triglyceride waste products, is thought to be a be a limiting factor in photodynamic fat reduction. Edema, due to congestion of the lymphatic system, is one of the reasons compression garments are suggested after non-invasive lipolysis procedures.

VanquishME™, produced by BTL Holdings, is a contact free RF diathermy device capable of fat reduction and skin tightening (Pub. No.: U.S. Pat. No. 9,468,774B2). Unlike PEMF devices, which employ low frequency electromagnetic fields typically under 100 Hz, RF diathermy generally use high frequency electromagnetic waves on the order of megahertz or gigahertz. VanquishME™ generates RF diathermy via high frequency electromagnetic waves in the range of 13.553-13.567 MHz, 26.957-27.283 MHz, 40.66-40.70 MHz, or 2.4-2.5 GHz. The electromagnetic field can be applied in continuous or pulse mode, and the applicator uses a coil as a source of the magnetic field.

The temperature of the skin surface is maintained between 32-45° C. Within that temperature range, there is permanent destruction to the adipocytes. In addition, there is heating of collagen fibers resulting in skin tightening. The device uses multiple treatment applicators, and is indicated for regions with cellulite, especially the buttocks, abdomen, hips, thighs and arms.

While the applicator is capable of treating multiple regions, including the abdomen and flanks simultaneously, the device has several disadvantages; it causes fat cell destruction, which can result in dysmorphic fat accumulation if the user later gains weight. Also, each application can only treat a limited area of the body, and the method causes the circumferential reduction in size only to the limited treated body area.

Vibration platforms, such as PowerPlate™ and Hyper-Vibe™ can help reduce bodyfat and cellulite. They also increase growth hormone, bone density, muscular strength and cardiovascular fitness. The vibration platform moves in a lineal (vertical-only) direction, vertical sea-saw motion, horizontal movement, or a combination of the three motions, and results in passive contraction of striated muscles. Studies show many types of vibration platforms are effective. Depending on the speed and intensity of the oscillations, different muscles in the body are passively stimulated. Muscle contraction enhances lymphatic flow and increases metabolism. The force of the vibrations, when distributed into subcutaneous tissues and cellulite, can help loosen fibrous bands and decrease edema, both of which contribute to the appearance of cellulite. The increase in muscle tone also tightens and firms the skin. Blood flow is enhanced by the vibration plate, especially combined with oxygen therapy: the combination increases the oxygen tension in the red blood cells, so they tend not to aggregate in clusters as they flow through the vascular system. Numerous clinical studies confirm the positive benefits of vibration platforms, however, there are several disadvantages to using a vibration platform as a passive and primary treatment for weight loss. Most notably, weight loss is slow, since the passive contractions burn an estimated 100-200 calories per session. As with all forms of exercise, visceral fat (especially around the liver) will be lost preferentially to subcutaneous fat, effecting less of a cosmetic enhancement.

Therefore, a need exists to overcome the problems with the prior art as discussed above.

SUMMARY OF THE DISCLOSURE

The disclosure provides a device and method for inducing lipolysis in humans that overcomes the hereinafore-mentioned disadvantages of the heretofore-known devices and methods of this general type and that combines various modalities of treatment using feedback control to optimize treatment as the various modalities are being applier to optimize their effect.

In accordance with the inventive disclosure, there is provided a device for inducing lipolysis in a living animal organism which can include at least one mounting element having a front surface, a plurality of light emitting elements disposed on the front surface that are configured to emit at least one selected wavelength of light, and at least one electromagnetic coil disposed on the front surface and configured to produce an electromagnetic field in a direction that is substantially perpendicular to the front surface. The device can further include a vibration platform that is configured to impart vibration into a body of the living animal organism while the living animal organism is being exposed to light from the plurality of light emitting elements and the electromagnetic field of the at least one electromagnetic coil. The device can still further include a controller operatively coupled to the plurality of light emitting elements, the at least one electromagnetic coil, and body vibratory. The controller is configured to control the plurality of light emitting elements, the at least one electromagnetic coil, and vibration platform according to a selected treatment regimen, and wherein at least a portion of the selected treatment regimen includes controlling the plurality of light emitting elements, the at least one electromagnetic coil, and body vibratory to act on the living animal organism simultaneously.

In accordance with a further feature, the at least one mounting element is a plurality of mounting elements that are configured to substantially surround the living animal organism on different sides of the living animal organism.

In accordance with a further feature, the plurality of light emitting elements are a plurality of light emitting diode (LEDs).

In accordance with a further feature, the plurality of LEDs are arranged in a plurality of LED groups, and wherein the plurality of LED groups are arranged in a matrix of rows and columns.

In accordance with a further feature, the at least one electromagnetic coil is configured around a border of the front surface of the at least one mounting element.

In accordance with a further feature, the at least one electromagnetic coil comprises a plurality of coils disposed on at least one mounting element.

In accordance with a further feature, at least some of the plurality of light emitting elements are configured to emit light having a wavelength of one of 405 nm, 440 nm, 532 nm, 590 nm, 635 nm, 650 nm, 850 nm, or 980 nm.

In accordance with a further feature, a first portion of the plurality of light emitting elements is configured to emit light at a first wavelength, a second portion of the plurality of light emitting elements is configured to emit light at a second wavelength, and a third portion of the plurality of light emitting elements is configured to emit light at a third wavelength, wherein the first wavelength, second wavelength, and third wavelength are all different wavelengths.

In accordance with a further feature, a negative ion generator can be included that is controlled to be operable during a treatment regimen.

In accordance with a further feature, the plurality of light emitting elements are controlled to output light according to a modulation waveform.

In accordance with a further feature, the electromagnetic field of the at least one electromagnetic coil is pulsed.

In accordance with a further feature, the electromagnetic field is produced having a frequency in a range of 0-45,000,000 Hertz.

In accordance with a further feature, the light emitted by the plurality of light emitting elements and the electromagnetic field produced by the at least one electromagnetic coil is adjusted during a treatment regimen based on feedback received by the device.

In accordance with a further feature, the device further includes a camera having a field of view, wherein the camera produces images of living animal organism in the field of view, and wherein the feedback comprises differences in successive images of the living animal organism during the treatment regimen.

In accordance with a further feature, the device further includes a network radio transceiver, wherein the network radio transceiver is configured to receive signals from a bio-impedance sensor, and wherein the feedback comprises changes in bio-impedance over time.

In accordance with some embodiments of the disclosure, there is provided a system that includes at least one mounting element having a front surface. The device further includes a plurality of light emitting elements disposed on the front surface that are configured to emit at least one selected wavelength of light, and a plurality of electromagnetic coils disposed on the front surface, each of which are configured to project an electromagnetic field in a direction that is substantially perpendicular to the front surface. The device further includes a controller configured to control the plurality of light emitting elements and the plurality of electromagnetic coils to combine a light output of the plurality of light emitting elements and an output of each one of the plurality of electromagnetic coils to induce lipolysis in a person, and induce a physiological effect in a person that simulates an effect of a pharmaceutical.

In accordance with another feature, the controller is configured to control the plurality of electromagnetic coils deliver one or more resonant electromagnetic frequencies derived from a physical sample, an "in silicon" ligand designed to interact with a target receptor or molecular target, or an "in silicon" bioactive protein computed using a Resonant Recognition Model that is derived from a desired structure and function of "in silicon" bioactive protein, or from a known DNA sequence that codes for an specific protein.

In accordance with another feature, the controller is configured to control the plurality of electromagnetic coils deliver one or more resonant electromagnetic frequencies derived from a nuclear magnetic resonance of the physical sample, the "in silicon" ligand, or the "in silicon" bioactive protein.

In accordance with another feature, the controller is configured to control the plurality of light emitting elements to localize the effect of the resonant electromagnetic frequencies.

In accordance with another feature, the controller is configured to control the plurality of electromagnetic coils to produce pulsed electromagnetic fields to localize the effect of the resonant electromagnetic frequencies.

Although the disclosure is illustrated and described herein as embodied in a device and method for inducing lipolysis in humans, it is, nevertheless, not intended to be limited to the details shown because various modifications and structural changes may be made therein without departing from the spirit of the disclosure and within the scope and range of equivalents of the claims. Additionally, well-known elements of exemplary embodiments of the disclosure will not be described in detail or will be omitted so as not to obscure the relevant details of the disclosure.

Other features that are considered as characteristic for the disclosure are set forth in the appended claims. As required, detailed embodiments of the present disclosure are disclosed herein; however, it is to be understood that the disclosed embodiments are merely exemplary of the disclosure, which can be embodied in various forms. Therefore, specific structural and functional details disclosed herein are not to be interpreted as limiting, but merely as a basis for the claims and as a representative basis for teaching one of ordinary skill in the art to variously employ the present disclosure in virtually any appropriately detailed structure. Further, the terms and phrases used herein are not intended to be limiting; but rather, to provide an understandable description of the disclosure. While the specification concludes with claims defining the features of the disclosure that are regarded as novel, it is believed that the disclosure will be better understood from a consideration of the following description in conjunction with the drawing figures, in which like reference numerals are carried forward. The figures of the drawings are not drawn to scale.

Before the present disclosure is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present disclosure, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present disclosure and simplify the description, but not to indicate or imply that the devices or components must have a specific azimuth, or be constructed or operated in the specific azimuth, which thus cannot be understood as a limitation to the embodiments of the present disclosure. Furthermore, terms such as "first", "second", "third" and so on are only used for descriptive purposes, and cannot be construed as indicating or implying relative importance.

In the description of the embodiments of the present disclosure, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. The terms "instruction code," "program," "software application," and the like as used herein, are defined as a sequence of instructions designed for execution on a computer system. "Instruction code," a "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system. Those skilled in the art can understand the specific meanings of the above-mentioned terms in the embodiments of the present disclosure according to the specific circumstances. Furthermore, such code is known to be performable on various computing platforms, not limited to embedded, mobile, and general purpose computing platforms. Such platforms can be distributed using networks where different computing systems that are physically remote from each other can cooperatively interact and process information in the form of data to accomplish a desired goal.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present disclosure.

DETAILED DESCRIPTION

Figure 1:
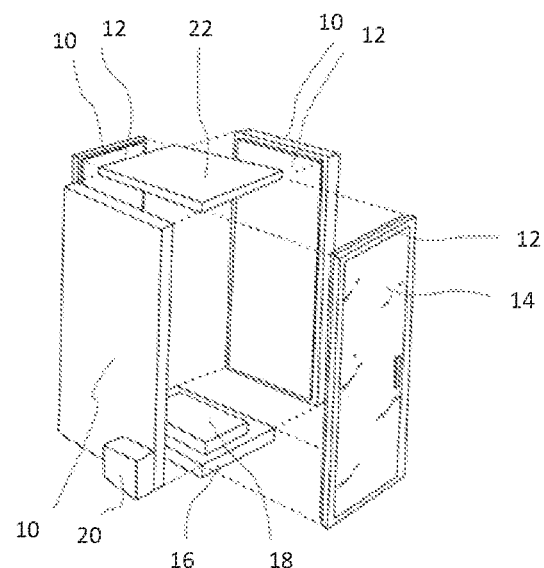
FIG. 1 is a perspective exploded view of a sauna device for inducing lipolysis, in accordance with some embodiments.

While the specification concludes with claims defining the features of the disclosure that are regarded as novel, it is believed that the disclosure will be better understood from a consideration of the following description in conjunction with the drawing figures, in which like reference numerals are carried forward. It is to be understood that the disclosed embodiments are merely exemplary of the disclosure, which can be embodied in various forms.

The present disclosure provides a novel and efficient device and method for inducing lipolysis in humans. Embodiments of the disclosure provide a device that combines various modalities of treatment known to induce lipolysis. In particular, the device can include light emitters that are configured to emit light at wavelengths know to induce lipolysis. In addition, embodiments of the disclosure provide electromagnetic field generating components that are configured to generate electromagnetic fields at varying frequencies that will induce lipolysis. Further, mechanical vibration components can be combined with these other components to enhance the effect of lipolysis generated by the other components. The output of the light and electromagnetic field generating components can be adjusted during treatment based on feedback relating to the response of the body of the person receiving the treatment.

In describing the frequency or frequencies of LED and laser light employed in different embodiments of the present disclosure, the peak frequency or frequencies of the LED and laser light will be listed; it is to be understood that the spectrum of light output of an LED or laser varies by at least +/−5 nm, and the variation depends on a variety of factors including manufacturing tolerances, random anomalies within batches of LEDs and lasers, operation temperature, etc. These variations, as well as the nomenclature of defining an LED or laser by its peak output frequency, is well known to those skilled in the art.

The inventive embodiments of the present disclosure provide a full-body fat reducing device and method that can utilize optical emitters, electromagnetic fields, mechanical vibrations, and topical creams. These elements can be synergistically combined in a treatment that can reduce body fat and reduce the appearance of cellulite. Referring now to FIG. 1, there is shown a light sauna 8 in accordance with some embodiments. The light sauna 8 represents some embodiments which include several walls 10 designed to surround a person receiving the treatment and act as panels which are mounting elements on which emitting components are mounted. Each one of the walls 10 can include one or more fixed LED or laser optical emitter arrays 12 on an inside of each wall 10 so as to emit light into the space contained within the walls 10. In the following description, while LED/LEDs are described, it will be understood that similar light sources can be used equivalently, including lasers. LEDs act as a descriptive surrogate for light sources that can be designed to emit light of specific, selected wavelength. Other examples of light sources that can be used include, for example, pulsed lasers (pico & femto second), and filtered white light sources.

In some embodiments there can be as few as two walls 10 joined together at 90 degrees to each other. A door 14 can be coupled to one of the walls or door frame that is coupled to two walls. In embodiments with a door 14 the door can act as a wall and can likewise include one or more LED optical emitter arrays. In embodiments include a door 14 there can be two or three other walls (for three or four total walls, effectively). As will be described, the LED optical emitter arrays 12 include LED elements that are configured to emit light at selected wavelengths that are known to affect lipocyte cells and related tissue. A ceiling 22 can be included in some embodiments that may comprise a mirror or an additional LED optical emitter array. In some embodiments a vibration platform 18 can be provided on a floor 16 of the light sauna 8. A user (e.g. patient or person receiving treatment) can stand on the vibration platform 18 during treatment, the vibrations produced by the vibration platform 18 can aid in the process of removing fat from the person's body. The vibration platform can be similar to those made by Hypervibe, LLC. In some embodiments an oxygen source or compressor 20 can be used to facilitate increased oxygen intake by a person receiving treatment in the light sauna 8 to further facilitate removal of fat from the person's body.

Figure 2:
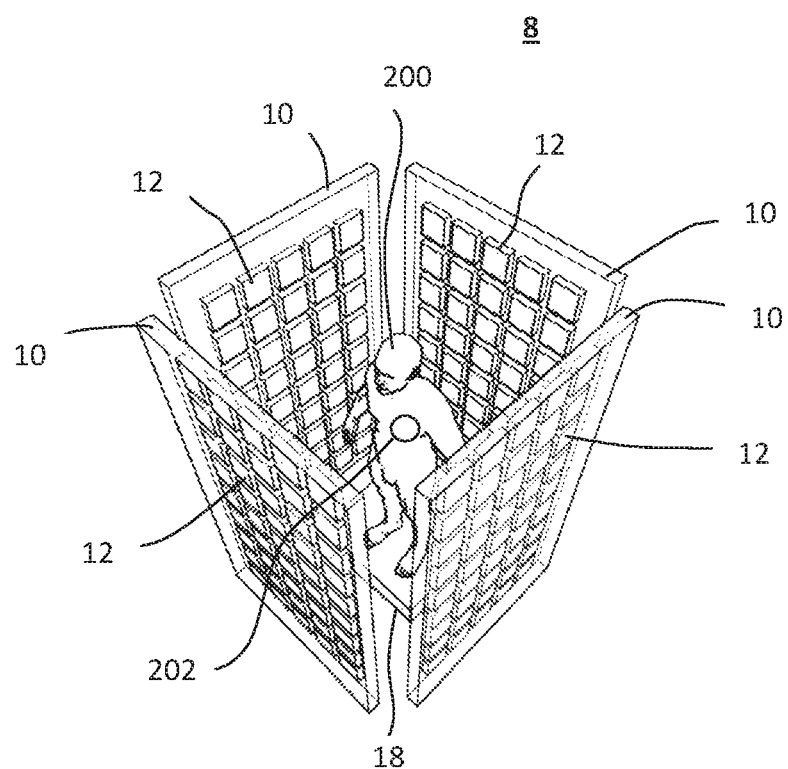
FIG. 2 is a perspective view of a portion of a sauna device for inducing lipolysis treating a user, in accordance with some embodiments.

FIG. 2 shows a light sauna 8 in which a human user 200 is positioned, in accordance with some embodiments. The light sauna 8 can be substantially similar to that of light sauna 8 of FIG. 1. Although the light sauna 8 is shown as having four sides (one of which can be a door), the light sauna 8 can take a multitude of configurations that surround an interior space including circular and octagonal. Each of the walls can include one or more LED optical emitter arrays 12. In some embodiments there can be multiple LED optical emitter arrays 12 on one or more walls 10. In some embodiments reverse cylindrical lens arrays and/or Fresnel lenses can optionally be employed to focus light output from the LED optical emitter arrays 12 onto the body of a user 200. In some embodiments, portions of the inside surfaces of the walls 10 that are not taken up by the LED optical emitter arrays 12 can be covered with a mirror surface to reflect light emitted by the LED optical emitter arrays onto the user 200. In general, a person can enter the sauna 8 with particular areas of their body exposed for treatment, and then the LED optical emitter arrays 12 can be activated to produce light at one or more selected wavelengths. In embodiments where the user 202 is surrounded by walls 10 with LED optical emitting arrays 12, the user can simply stand in place during the treatment duration. In embodiments using two walls 10 that are joined together at 90 degrees to each other, the user 200 can stand still for a treatment duration to expose one side their body, and then turn one hundred eighty degrees to expose the other sides of their body. In some embodiments the user 200 can have a bio-impedance sensor 202 adhered to their skin. The bio-impedance sensor can determine the electrical of the tissue/skin of the person to whom the bio-impedance sensor is attached. Impedance over time during the treatment, which will change with changes in the fat in the portion of the user's body being sensed. In some embodiments multiple bio-impedance sensors can be used on respective different portions of the user's body. The bio-impedance can be monitored during application of treatment, and output of the light and/or electromagnetic field generating components can be adjusted based on changes in bio-impedance during treatment.

Figure 3:
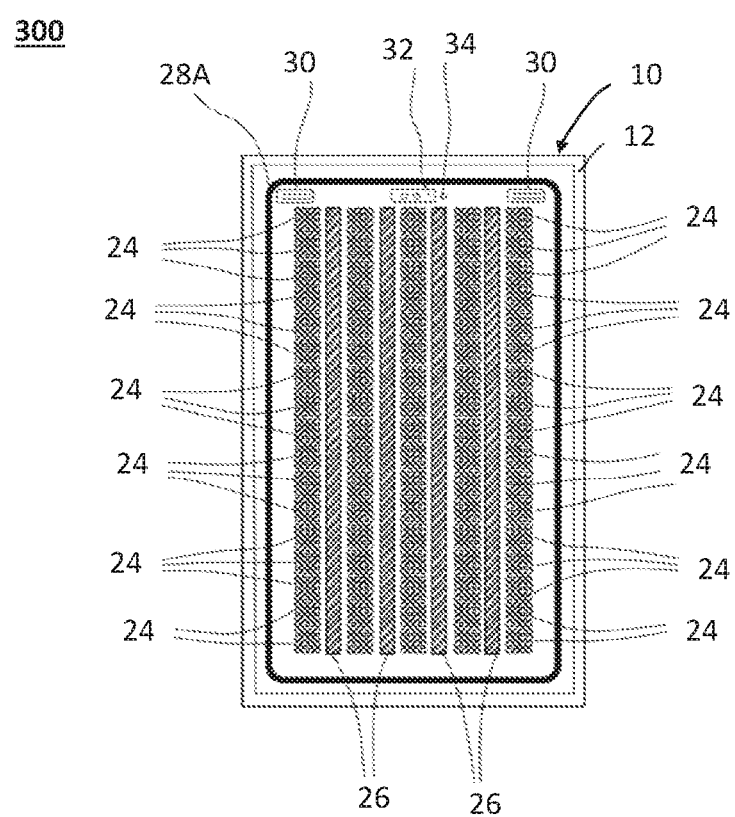
FIG. 3 is elevational view of a user-facing side of a panel for inducing lipolysis, in accordance with some embodiments.

FIG. 3 shows the inside of a wall 10 that include an LED optical emitter array 12, in accordance with some embodiments. The LED optical emitter array 12 include a plurality of LEDs 24 that can be organized into groups, such as groups of rows and columns or other grouping arrangements. A conductor coil 28a can be disposed around the border of the inside surface of the wall 10, encircling all of the other components. The conductor coil 28a is coupled to a power supply that can produce a current, or current pulses, to be conducted through the coil, thereby generating an electromagnetic field, or a pulsed electromagnetic field. As is known, when current circulates through the coil as shown, which defines a plane that is coplanar with the page of the drawing, the resulting electromagnetic field will include a component that is perpendicular to the plane of the coil 28a, meaning the electromagnetic field will be directed to the interior of the sauna and a person in the sauna. or adjacent/in front of the wall 10. As will be discussed, it has been found that electromagnetic fields are useful in stimulating muscle tissue.

The wall 10 can include one or more negative ion generators 30 that can enhance the effect topical substances which themselves are used to increase the efficacy of the light, electromagnetic fields, and vibration. A camera 32 can be a stereoscopic camera that is used to judge the position of person inside the sauna, and in particular their distance from the wall 10. This is information can be used to adjust the output of the LED optical emitters and the electromagnetic field. A thermal sensor 34 can also be used to determine a skin temperature of a person in the sauna proximate to the wall 10. In a sauna there can be more than one wall 10, and each wall will be configured with a plurality of LED groups 24. One or more walls can have vents 26, an electromagnetic coil 28a, negative ion generators 30, a camera 32, and a temperature sensor 34. In some embodiments the camera 32 can be used for image-based feedback such as by comparing successive images taken periodically during treatment to identify changes in body tissue response to the treatment, including, among others, temperature of the skin/tissue, proximity of the body to the output elements (light and electromagnetic field).

The wall 10 can include one or more air vents 26 that provide ventilation by forced air convection or from an external air conditioning unit. As shown, the air vents 26 are arranged in columns between columns of LED groups 24 to ensure even coverage of both light emitted from the LEDs 24 and air from the vents 26. As shown here, the vents 26 are the external grill portion of the air handling system. The grills prevent inadvertent intrusion, such as by a finger or other body part, into the ventilation system. In some embodiments the grills can include moveable element that can be adjusted to direct air into a desired direction.

Figure 4:
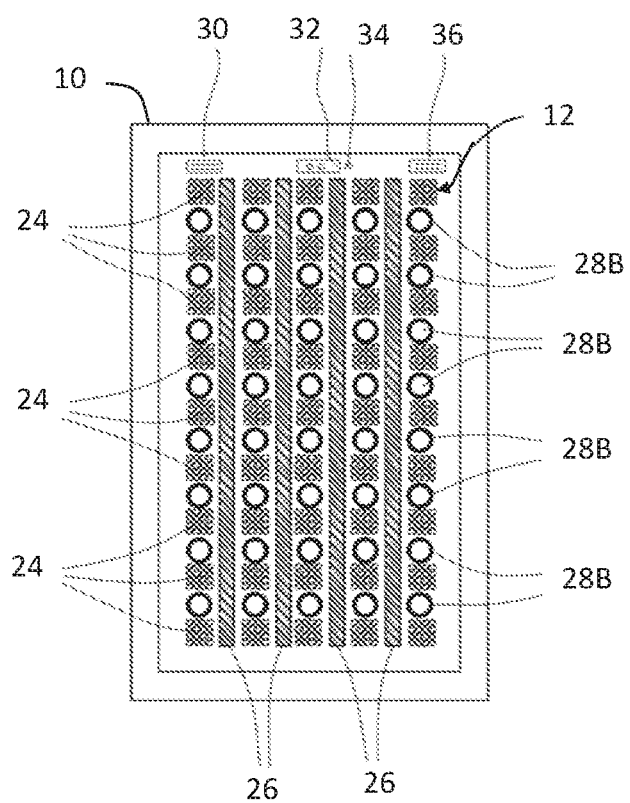
FIG. 4 is elevational view of a user-facing side of a panel for inducing lipolysis, in accordance with some embodiments.

FIG. 4 shows a wall 10 having an LED optical emitter array 12 including a plurality of LED groups 24. As in FIG. 3, the LED groups 24 each include a plurality of LEDs that are configured to emit one or more specific wavelengths of light. In general LEDs can be configured to emit light in a narrow band of the light frequency spectrum. Thus, light can be emitted at a desired wavelength/frequency within some tolerance (e.g. +/−5%). However, it is known that after manufacturing, LEDs can be tested and sorted by wavelength so that even narrower tolerances can be achieved. Also similar to FIG. 3, the wall 10 of FIG. 4 can include negative ion generators 30, a camera 32, and an optical thermal sensor 34. Differing from FIG. 3, however, is the arrangement of electromagnetic coils 28b. Whereas, in FIG. 3, coil 28a is a single coil disposed around the major surface of the wall, substantially following the border/edges of the wall 10 in FIG. 3, in FIG. 4 there is a plurality of smaller coils 28b forming a matrix where the coils 28b are interspersed between LED groups 24 in each column of LED groups 24 and coils 28b. Each of the columns of LED groups 24 and coils 28b are separated by vents 26. In this arrangement, individual coils 28b can be controlled to output different magnetic field strength as each coil 28b will correspond, in vertical and lateral positioning, with a different portion of a person's body, and that correspondence will change from person to person, generally. Accordingly, for example, camera 32 can be used to obtain spatial measurements of the person's body, and their proximity to the wall 10. This spatial information can be used to control each coil 28b to output a selected magnetic field strength (or pulsed strength) based on the person's proximity to the wall at various vertical and horizontal points of the wall 10.

The optical energy output of the LED optical emitter arrays 12 of FIGS. 3-4 will be generated by a plurality of LED in the LED groups 24 which cumulatively produce light at, in some embodiments, approximately wavelengths of 635 nm, 850 nm, and 980 nm, at an intensity of approximately 10,000-200,000 Lux for 635 nm light, measurable at each LED optical emitter array. The intensity of 850 nm light and 980 nm light will both be between 20 mw/cm$^2$ to 1000 mw/cm$^2$. These wavelengths have been found to be particularly useful in promoting lipolysis in humans. In some embodiments the LED optical emitter arrays can be configured to emit light at 405 nm, 440 nm, 532 nm, and/or 590 nm which affects cytochrome C. In particular 405 nm and 440 nm affect the melanopsin/TRPC channel axis, 532 nm light affects the TRPV1 receptor, and 590 nm light affects the B3 receptor.

A pulsed electromagnetic field (PEMF) generator can be used to provide current to the coils 28a, 28b that are mounted on the wall 10 and the door 14. The output of the PEMF generator, and therefore the coils, can be controlled by a microcontroller and amplifier/power supply. The coils 28a, 28b can be either air core, magnetic core, or a combination of both, and magnetic focusing lenses can be employed. The coils can be driven at a constant current, or more preferably by a current waveform composed of one or more frequencies generated by the PEMF generator. In some embodiments the modulation frequencies of the PEMF generator can be as low as 0.01 Hz, and up to 30 GHz. In some embodiments the PEMF generator can control the current waveform to have a fundamental frequency one of the Rife Frequencies, Solfeggio tone frequencies, and/or Schuman Frequencies. In some embodiments the PEMF generator can drive the coils 28a, 28b at 50 Hz. In some embodiments the PEMF generator can drive the coils 28a, 28b at 1.618 Hz, 10 Hz, 20 Hz, 50 Hz, 500 Hz, 900 Hz, 1000 Hz and/or 1100 Hz. The coils 28a, 28b can also be operated at radio frequencies (RF) to generate radio diathermy for increased skin tightening. Lymphatic drainage can be enhanced using the PEMF generator and coils 28a, 28b to effect calcium release from the sarcoplasmic reticulum of muscle cells of a person being subject to magnetic fields varying at these frequencies, which can also induce passive contractions in both smooth muscle and striated muscle which will result in firming of the muscles.

The light output level of the LEDs in LED groups 24 can be controlled out output light according to a modulation waveform by modulating the current provided to the LEDs. That is, a signal can be superimposed on a direct current (DC) that is sufficient to ensure that the LEDs remain sufficiently forward biased to emit light, and a varying signal on top of the DC current will then produce a corresponding variation in the light output of the LEDs, subject to the non-linearity of the diode junction which can be taken into account when selecting a waveform to superimpose on the DC current. In some embodiments, for LEDs configured to emit light at a wavelength of 635 nm, a modulation frequency of between 0.01 Hz and 4,000,000 Hz can be used. In some embodiments a modulation frequency of 80 Hz and/or or 300 Hz can be used. In some embodiments a modulation frequency can be selected from 292 Hz, 584 Hz, 1,168 Hz, and 2,336 Hz frequencies. When other, non-LED light sources are used, equivalent power modulation can be used to achieve a substantially similar effect.

LEDs configured to emit a wavelength of 850 nm can be driven at a straight constant current (no AC component superimposed). In some embodiments an AC signal composed of one or more frequencies between 0.01 Hz and 4,00,000 Hz can be superimposed on the DC. In some embodiments a frequency of 40 Hz, 292 Hz, 584 Hz, 1,168 Hz, or 2,336 Hz can be used with these LEDs.

LEDs configured to emit a wavelength of 980 nm can be driven at a constant DC. In some embodiments these LEDs can be driven with a signal including components of one or more frequencies between 0.01 Hz and 4,00,000 Hz. In some embodiments these LEDs can be driven with a frequency of 40 Hz, 292 Hz, 584 Hz, 1,168 Hz, or 2,336 Hz.

The waveforms controlling the output of the 635 nm LEDs, 850 nm LEDs, and 980 nm LEDs can be generated by a microcontroller or a controllable signal generator.

Figure 5:
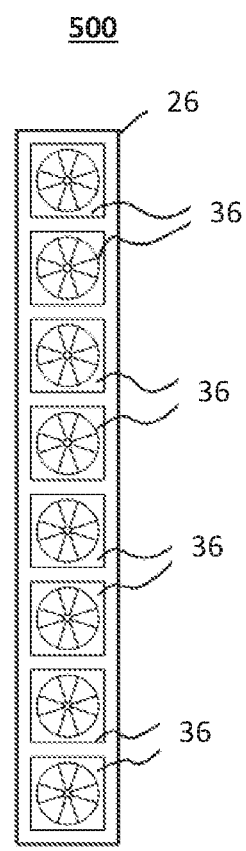
FIG. 5 is view of a column of fan units that can be located behind a vent in a panel for inducing lipolysis, in accordance with some embodiments.

FIG. 5 shows a ventilation unit 500, in accordance with some embodiments. The ventilation unit 500 is columnar, and sits behind a grill of a vent 26 such as that shown in FIG. 3. The ventilation unit can be comprised of one or more fan units that each have a fan 36 that force air through the vents 26. In some embodiments a speed of the fan 36 can be selectively controlled to a desired speed setting as well as a desired air temperature setting.

Figure 6:
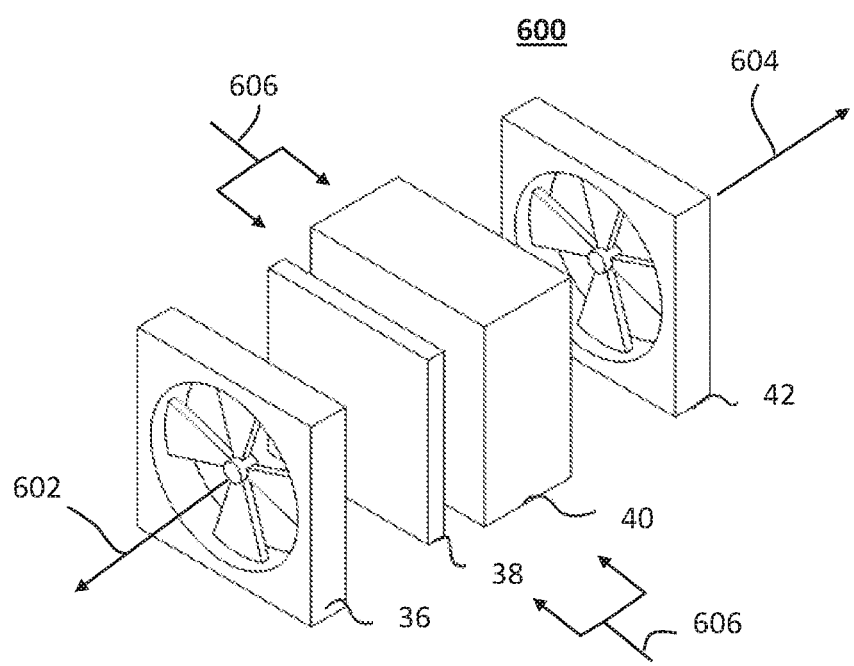
FIG. 6 is an exploded perspective view of a fan unit for producing a temperature controlled air flow in conjunction with a device for inducing lipolysis, in accordance with some embodiments.

FIG. 6 shows a fan unit 600, in accordance with some embodiments. The fan unit 600 includes a fan 36 that is positioned adjacent a cooling element 38 that can be, for example, an electrothermic device such as a Peltier device. The cooling element 38 cools air at a front side (towards fan 36). Air can be pulled in from the sides (which can include the top and bottom) as indicated by arrows 606. The fan 36 blows cool air from the cooling element 38 in the direction of arrow 602, into the interior space of a light sauna (e.g. 8 of FIG. 1). The cooling element 38 operates by drawing heat energy from its front side to its back side, which is opposite the front side. The cooling element 38 can be mounted to a heat sink 40 at the backside of the cooling element 38. The heat sink 40 conducts heat away from the back side of the cooling element 38. Thermal energy conducted into the heat sink 40 is transferred outside the sauna via convection from a secondary fan 42 mounted adjacent to the heatsink that is oriented to blow air in the opposite direction from that of fan 36, as indicated by arrow 604. Thus, by using cooling element 38, and providing multiple fan units 600, chilled air can be blown into the interior of the sauna. The benefit of using thermoelectric cooling elements is that the electric current can be reversed to achieve a heating effect instead if it is so desired. However, in order to optimize the penetration of selected light wavelength(s) emitted by the LED optical emitter units, it is desirable to expose the person in the sauna to chilled air as this causes the body to naturally constrict blood vessels near the surface of the skin, allowing the light penetrate deeper into the person's tissue and reach adipose tissue and lipocyte cells.

Before using the lipolysis sauna apparatus 8, one or more topical products may be applied for the following purpose and/or purposes: enhance lipolysis, reduce cellulite, increase collagen, decrease hair growth and/or thickness on the body and/or face, increase hair growth and/or thickness on the head, and positively influence skin tone. The topical products may be creams, lotions, emulsions, gels, serums, sprays, or other forms allowing broad or narrowly focused application on the human body. Micro needling of skin surfaces can be employed optionally to increase absorption and penetration depth of the topical products. The topical product, or combination of products, may contain the following:

Mitochondrial uncoupling agents (one or any combination of the following may be employed): fucoxanthin, brown seaweed extract, methyl-salicylate, trolamine salicylate, white willow bark, any other salicylic acid derivatizes, N-acyl amino acids, ortho-Carborane, oleanolic acid, 2,3-dinitrophenol, colloidal silver, anti-fungal medications, and any other mitochondrial uncoupling agent known to those familiar with the art;

Beta agonists (one or any combination of the following may be employed): theophylline, aminophylline, caffeine, albuterol, clenbuterol, Mirabegron, cocaine, amphetamine salts, methamphetamine, methylphenidate, Benzedrine, MMDA, and any other beta agonist known to those familiar with the art;

Antioxidants (one or any combination of the following may be employed): green tea extract, CBD oil, black tea extract, resveratrol, vitamins A, D, E, and K, Vitamin C, glutathione, grape seed extract, *Sambucus Nigra* fruit extract, Squalane, and any other antioxidant agent known to those familiar with the art;

Thermogenic enhancers (one or any combination of the following may be employed): menthol, forskolin, grapefruit extract, capsaicin and/or any of its derivatives, Evodiamine, YY-312 (herbal extract powder from *Imperata cylindrica* Beauvois, Citrus unshiu Markovich, and Evodia *officinalis* Dode), vanilloid receptor agonists, vanilloid receptor antagonists (which result in increased production of natural vanilloid receptor agonists), retinol and/or any other vitamin A derivative, berberine, coconut oil, spearmint oil, cinnamon and/or any of its derivatives, limonene, licorice extract, and any other thermogenic enhancing agent known to those familiar with the art;

Skin texture enhancers (one or any combination of the following may be employed): hyaluronic acid, alpha hydroxy acid, beta-hydroxy acid, glycolic acid, lactic acid, collagen peptides, Epidermal Growth Factor, Caprylic/Capric Triglyceride, peppermint oil, Cabbage Rose extract, and other peptides and chemicals to enhance skin texture known to those familiar with the art;

Skin tone equalizer (one or any combination of the following may be employed): hydroquinone, steroids, retinoic acid, kojic acid, arbutin, niacinamide, glutathione, haloxyl, Ascorbyl Tetraisopalmitate, grape extract, mulberry extract, milk enzymes, Saxifraga extract, saffron extract, licorice extract, Kumkumadikeram, Manikya Bhasma, mercury and any skin lightening agent or skin tone equalizer known to those familiar with the art;

Cellulite reduction enhancers (one or any combination of the following may be employed): ALCAR, l-carnitine, l-carnitine derivatives, l-citrulline, phosphatidylcholine, *glycyrrhiza* extract, Furcellaria lumbricalis, Fucus vesiculosus, retinoid, conjugated linoleic acid (CLA), PEGylated conjugated linoleic acid (PCLA), glaucine, AdipoSlim, caffeine, retinyl palmitate, Provislim (fisetin and frambinone), Centella *Asiatica* Extract, *Ginkgo Biloba* extract, bitter orange extract, chlorophyllin-copper complex, Grapeseed oil, *Eucalyptus* oil, Lemon oil, Grapefruit Oil, and any other cellulite reducing agent known to those familiar with the art;

Hair growth retardants (one or any combination of the following may be employed): eflornithine, *Curcuma aeruginosa*, rosemary oil, and any other hair growth retardant agent known to those familiar with the art;

Nitric oxide enhancers (one or any combination of the following may be employed): horny goat weed, pygnogenol, PDE-5 inhibitors, nitrates, and any nitric oxide source or augmenting agent known to those familiar with the art;

Photosensitizers (one or any combination of the following may be employed): indocyanine green, malachite green, gold nanoparticles, silver nanoparticles, tourmaline powder and/or nanoparticles, jade powder and/or nanoparticles carbon nanoparticles, and any photosensitizing agent known to those familiar with the art;

Lymphatic drainage enhancers (one or any combination of the following may be employed): ocotillo bark, stillingia root, *astragalus*, ginger root, Mullein Leaf, Bayberry Root Bark, Clivers Aerial Parts, Plantain Leaf, Alfalfa Aerial Parts, Chamomile Flowers, *Echinacea Purpurea* Root, Yarrow Aerial Parts, Garlic Bulb, Red Root, *Lobelia* Aerial Parts, Sodium Copper Chlorophyllin, Galium apertines, calendula, devil's claw, Dandelion root, yellow dock root, burdock root, goldenseal, nettles, parsley, myrrh, licorice root, goldenseal, *echinacea*, prickly ash bark, manjistha, bupleurum, rehmannia, and any lymphatic drainage enhancing agent known to those familiar with the art;

Anti-inflammatory agents (one or any combination of the following may be employed): *arnica*, salicylates, curcumin and curcumin derivatives, turmeric, black pepper extract, NSAIDs, dexamethasone, hydrocortisone, and any anti-inflammatory agent known to those familiar with the art; and Mitochondrial enhancers: methylene blue, or similar agents known to those familiar with the art.

An additional topical product containing ingredients to increase the optical penetration of light into tissue, may also be applied. One study has proven that glycerol applied 20 minutes before phototherapy can be used for this purpose as it causes water molecules to move out of skin and subcutaneous tissue. Glycerol is a large molecule and osmotically active. As water moves out of cells, they shrink, and light energy can penetrate deeper into adipose tissue. Interestingly, the dehydration of tissues is reversed without further manipulation. Eventually, glycerol diffuses into cells, and then draws water back into the cells. Other ingredients may also be employed to increase optical penetration. Caffeine, for example, will effect tissue dehydration and increase light penetration. Other osmotic agents, and metabolic enhancing agents, including but not limited to the xanthine class and similar agents known to those familiar with the art may be employed.

Alternatively, a topical product, or combination of the products, may be applied post-treatment. Such post-treatment application should occur within about 1-60 minutes after use of the light sauna 8 or similar apparatus. A topical hair growth formula containing one or more of the following may also be applied before treatment and/or after treatment:

Minoxidil;

DHT-blockers: dutasteride, finasteride, synthetic and herbal DHT-blockers known to those familiar with the art;

Jak-stat inhibitors: synthetic Jak/stat inhibitors including but not limited to tofacitinib, baricitinib, ruxolitinib and decernotinib, herbal Jak-Stat inhibitors including Brevilin A, Cucurbitacin B, JSI-124, Methoxydalbergione (4-MD), Curcumin, Thymoquinone (TQ), Acetoxychavicol acetate (ACA), Guggulsterone (GS), Hydroxy-2-methyl-1,4-naphthoquinone (plumbagin), Farnesol (FOH), Capillarisin (CPS), Nimbolide (NL), Shogaol (6SG), Sugiol, aminophylline (CTS), Alantolactone, (6,7-dimethoxycoumarin) other Jak/Stat inhibitors known to those familiar with the art;

Caffeine;

Rosemary oil; and

L-arginine.

In some embodiments the sauna device can employ either the fans 36 or other means for cooling the entirety or selected locations on the human body. Such cooling can increase optical penetration into human body tissues and hence the effective reduction of fat or the reduction of the appearance of cellulite. In some embodiments the sauna device can include an oxygen compressor 20 (e.g. in FIG. 1) that concentrates oxygen from room air and delivers it to the user 200 via a nasal canula in order to enhance aerobic respiration during treatment. In some embodiments the sauna device can include one or more negative ion generators 30 (e.g. in FIGS. 3-4) that can aid in electroporation, which can enhance absorption of topical products, as well as provide negative electrons directly to the mitochondrial chain where they can act as an antioxidant. Negative charge at the mitochondrial chain can neutralize reactive oxygen species (ROS) that limit aerobic respiration and the effect of photo modulation of cytochrome C (element IV of the respiratory chain). The chemical reaction of the free electrons (e) supplied to the mitochondria can be summarized as follows: $e^- + ROS. \rightarrow H_2O + O_2$.

In some embodiments LEDs that are configured to emit light at a wavelength of 525-530 nm can be included. Light at this wavelength can deliver light energy to hemoglobin, cutaneous tissue, subcutaneous tissue, adipose tissue and cellulite. Such LEDs for this wavelength can be included in one or more LED groups 24, or one or more of the LED groups 24 can be composed entirely of LEDs configured to emit light at this wavelength. In some embodiments the sauna device will employ only LEDs that produce light having a wavelength in the range of 405 nm, and no LEDs of other wavelengths. In some embodiments the sauna device will employ only LEDs that produce light having a wavelength in the range of 430-440 nm, and no LEDs of other wavelengths. In some embodiments the sauna device will employ only LEDs that produce light having a wavelength in the range of 525-530 nm, and no LEDs of other wavelengths. In some embodiments the sauna device will employ only LEDs that produce light having a wavelength in the range of 590 nm, and no LEDs of other wavelengths. In some embodiments the sauna device will employ only LEDs that produce light having a wavelength in the range of 635 nm, and no LEDs of other wavelengths. In some embodiments the sauna device will employ only LEDs that produce light having a wavelength in the range of 660 nm, and no other wavelengths. In some embodiments LEDs of all of these wavelengths can be combined and selectively activated to turn on only LEDs of one, two, three, four, five, six, or seven wavelengths, depending on the person and the therapy regimen being applied.

In some embodiments it is contemplated that the vibration platform (e.g. 18) can incorporate a coil driven by a PEMF generator to generate a vertical electromagnetic field. The vertical electromagnetic field can, like that generated by the horizontally oriented coils, be driven at a selected frequency or frequencies.

In some embodiments a bio-impedance sensor (e.g. 202) can be used to monitor lipolysis and/or provide data to the microcontroller. The microcontroller can use this feedback information to modulate output from any combination of the sauna device's systems, including the LED arrays 12, the coil 28a or array of coils 28b, and/or the vibration platform 18. In addition, or as an alternative to bio-impedance sensors, three dimensional cameras 32 (e.g. FIGS. 3-4) and/or ultrasonic emitters and receivers in discreet elements or arrays can be employed on one or any combination of the sides/walls 10 of the sauna device 8 to create three dimensional imaging of the body, and this data can be used as feedback by the microcontroller to modulate output from any combination of the device's system, including the LED arrays 12, the coil 28a or array of coils 28b, and the vibration platform 18. One or more infrared cameras 34 may be employed on each side/wall 10 of the sauna 8 to monitor skin temperature, and the resulting skin temperature data may be used by the microcontroller to control and modulate the output of any combination of the cooling system (e.g. FIG. 5), the coil 28a or array of coils 28b, which can be capable of RF diathermy, and LED emitters 24 in order to maintain skin temperature at optimum temperature to facilitate lipolysis. Maintaining skin temperature below 40 degrees Celcius (C) ensures non-destructive lipolysis (i.e. lipolysis occurs via light-induced lipolysis and electroporation, the latter of which allows fat contents to drain into the lymphatic system without permanent damage to adipocytes). Keeping skin temperature around 48-49 deg. C allows destructive lipolysis (i.e. the thermal energy destroys adipocytes, and the debris is cleared by the lymphatic system) without thermal damage to other tissue types, including but not limited to skin, muscle, nerve, and bone tissue. In either temperature range, thermal energy is delivered to the elastic fibrous tissue that is one major cause of the "orange peel" surface texture of cellulite; thermal relaxation of the fibrous bands is known to decrease the appearance of cellulite and improve tissue texture. Both temperature ranges deliver thermal energy to collagen and connective tissues within the dermal layers, promoting skin tightening and decreasing skin laxity.

Another embodiment of the present disclosure provides a novel method of diathermy due to the cumulative and synergistic effect of seven mechanisms: I) chemical diathermy from application of topical products (raises cutaneous and subcutaneous temperature by 2-3 deg. C); II) mechanical friction in body tissues induced by the vibration platform; III) heat generated by passive muscular contractions induced by PEMF; IV) heat generated by passive muscular contractions induced by standing on the vibration platform; V) a portion of the light output from the LEDs intended for photo modulation will be converted into heat as it is absorbed by melanin, cutaneous tissue, and subcutaneous tissues; VI) light energy above 980 nm that uses water as a chromatophore heats tissue as its mechanism of action; and VII) RF diathermy generated by the electromagnetic coils. By employing so many mechanisms for diathermy, the process is safer. Simply wearing cotton garments or other blocking covers where diathermy is undesirable will block enough light/photo radiation so that significant diathermy is prohibited.

Another embodiment of the present disclosure can employ LED optical light emitter arrays 12 delivering one or all of the following frequencies of light in continuous or pulsed modes: violet light (within the spectrum of 400-420 nm wavelength) and/or blue light (within the spectrum of 420-490 nm wavelength) delivering light energy to superficial skin, sebaceous glands, and hemoglobin in blood; green light (within the spectrum 490-570 nm wavelength) delivering light energy to hemoglobin, cutaneous tissue, subcutaneous tissue, adipose tissue and cellulite; orange/yellow light (within the spectrum of 570-620 nm wavelength) delivering light energy to the cutaneous tissue, subcutaneous tissue, superficial lymphatic ducts, adipose tissue, and cellulite; red light (within the spectrum of 620-700 nm wavelength) delivering light energy to the cutaneous tissue, subcutaneous tissue, superficial lymphatic system, adipose tissue, and cellulite; NIR light (within the spectrum of 700-1000 nm wavelength) delivering light energy to the cutaneous tissue, subcutaneous tissue, adipose tissue, and cellulite, lymphatic system, fascia, muscles, testicles (in men), and thyroid gland; IR light (within the spectrum of 1000 nm-10,000 nm wavelength) delivering light energy to the cutaneous tissue, subcutaneous tissue, adipose tissue, and cellulite. As an alternative or to augment the blue light band, an orally ingested supplement or pharmaceutical agent increasing nitric oxide may be used, including but not limited to: sodium nitrate, amyl nitrate, PDE-5 inhibitors, acetyl-L-carnitine, l-arginine, l-citrulline, horny goat weed, and pygnogenol. The pulse, duty cycle, and phase of the LED light emitters at each of the various wavelengths can be determined either simultaneously or independent of application to a particular patient. The light may be produced by a combination of LED, laser, carbon fiber, incandescent bulb, halogen bulb, or any other light sources. Additionally, the sauna can also include transmitters for UV light (280-400 nm wavelength) for nitric oxide-mediated vasodilation and increased oxygen delivery, increased vitamin D levels, and concomitant treatment of psoriasis, vitiligo, atopic dermatitis and localized scleroderma.

Another embodiment of the present disclosure also contains a magnetic core or noble-gas antenna to deliver into the sauna, and the human user therein, frequency-specific electric microcurrent without the need for direct contact via electrodes. A microprocessor can generate a single frequency or combination of frequencies in the range of 0.01 Hz-45,000,000 Hz, which is delivered to a power amplifier, and finally a noble-gas rod antenna that is placed in proximity to the person receiving treatment in the sauna. The waveforms can be any combination of ramped square wave, square wave, sine wave, polarized, or alternating direct current. Alternatively, the waveforms may be pre-recorded and provided by an internal or external audio source, including but not limited to an MP3 player or CD player. The electric current induced into human tissues will range between 1 picoamp to 50000 microamp in order to decrease inflammation, increase protein synthesis in muscle tissue, and heal injuries to cartilage, tendons, and bone. As an alternative, these currents can be induced using the PEMF coil 28a or array of PEMF coils 28b.

Figure 7:
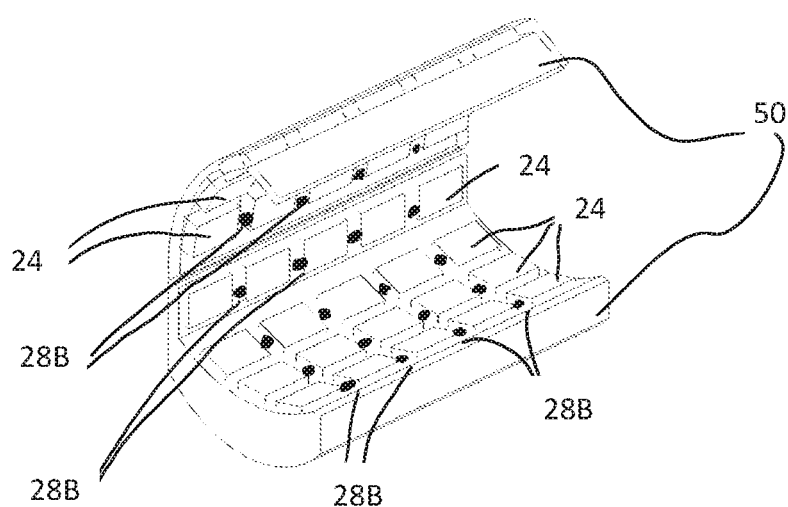
FIG. 7 is a perspective view of a device for inducing lipolysis in which a person can lay during treatment, in accordance with some embodiments.

FIG. 7 shows a light therapy bed 50 in which the human user patient lies on a flat or curved surface, in accordance with some embodiments. The light therapy bed 50 can include LED emitters 24 as well as one or more electromagnet coils 28b that can be driven with pulsed current to create pulsed electromagnetic fields. Multiple coils 28b with or without iron cores and magnetic lenses can be employed. Both the sides and the top of the patient can be covered with additional panels containing LED emitters. Alternatively, a curved structure containing LED elements may be employed to illuminate the sides and front of the user. Vibrations for lymphatic draining may be delivered through either a mechanical or acoustic vibration panel under the surface on which the patient lies; alternatively, lymphatic drainage may be enhanced using the PEMF coil(s) to effect calcium release from the sarcoplasmic reticulum of muscle cells, thereby inducing passive contractions in both smooth muscle and striated muscle. Vibration can be provided by transducers including, for example, piezo electric elements, Chaldni plates, or the equivalent. In some embodiments the transducers can be arranged to be in contact with the body of the person in the bed (or other device configuration), or they vibration can be air coupled, or both. Ultrasonic acoustic vibrations can be generated and focused on the person being treated. A three dimensional waveguide can be affixed to one or more of the transducers to produce an acoustic hologram. Alternatively, a plurality of vibroacoustic elements may produce sonic or ultrasonic holograms computed using mathematical transforms well known to those familiar in the art. The hologram may produce static acoustic images or vary with time. The acoustic hologram produced by the transducer or plurality of transducers may localize vibration to one or more specific locations in the body or space surrounding the body. One or more frequencies produced by the acoustic hologram can be at the resonant frequency of the human body, including the entire body, a specific organ, a specific tissue type, a specific cell type, a specific receptor, a protein, carbohydrate, or fat, or any molecule that is a structural element of a cell. The vibrations can be capable of inducing thermal energy to increase reaction rates, enhancing or disrupting physiological processes, or inducing thermal damage to a structure. This damage can include, but is not limited to, disruption of cell membranes in fat cells resulting in cavitation and necrosis of the fat cell, microtrauma to bone in order to activate osteoblasts and increase bone density, microtrauma to collagen fibers in order to induce increased collagen production and skin tightening, or microtrauma to glucose-amino-glycoside cross linkages to reduce somatic dysfunction. The term "somatic dysfunction" is used here in accordance with the textbook "Foundations of Osteopathic Manipulation, 6$^{th}$ edition" and is well understood by those skilled in the art of Osteopathic Manipulative Medicine.

A combination PEMF/acoustic vibration panel may be employed rather than discrete elements. Bio-impedance sensors can be employed to monitor lipolysis and/or provide data to the microcontroller to modulate output from any combination of the device's system, including the LED arrays, PEMF generator, and vibration platform. As an alternative to bio-impedance sensors, three dimensional cameras and/or ultrasonic emitters and receivers in discreet elements or arrays can be employed on one or any combination of the inner surfaces, such as the sides 10 of the device to create three dimensional imaging of the body. Additionally, the device may or may not include a magnetic core or noble-gas antenna or antennas to deliver frequency specific microcurrent without the need for direct contact via electrodes. A microprocessor will generate a single frequency or combination of frequencies in the range of 0.01 Hz-45,000,000 Hz, which is delivered to a power amplifier, and finally a magnetic core or noble-gas rod antenna. Alternatively, the waveforms may be pre-recorded and provided by an internal or external audio source, including but not limited to an mp3 player or CD player. The frequency specific microcurrents can alternatively be induced through the PEMF coils instead of a magnetic core or noble-gas antenna. RF diathermy may also be generated via the PEMF coils or antenna. Ventilation may be provided by forced air convection or an external air conditioning unit or Peltier devices to cool the skin. A negative ion generator can be included in the cooling system, or external to the cooling system. One or more infrared cameras or sensors may be employed to monitor skin temperature and modulate any combination of the cooling system, PEMF, RF diathermy, and light output in order to maintain skin temperature at physiogic levels. Maintaining skin temperature below 40 C ensures non-destructive lipolysis (i.e. lipolysis occurs via light-induced lipolysis and electroporation, the latter of which allows fat contents to drain into the lymphatic system without permanent damage to adipocytes.) Keeping skin temperature around 48-49 C allows destructive lipolysis (i.e. the thermal energy destroys adipocytes, and the debris is cleared by the lymphatic system) without thermal damage to other tissue types, including but not limited to skin, muscle, nerve, and bone tissue. In either temperature range, thermal energy is delivered to the elastic fibrous tissue that is one major cause of the "orange skin" appearance of cellulite; thermal relaxation of the fibrous bands is known to decrease the appearance of cellulite and improve tissue texture. Both temperature ranges deliver thermal energy to collagen and connective tissues within the dermal layers, promoting skin tightening and decreasing skin laxity.

Figure 8:
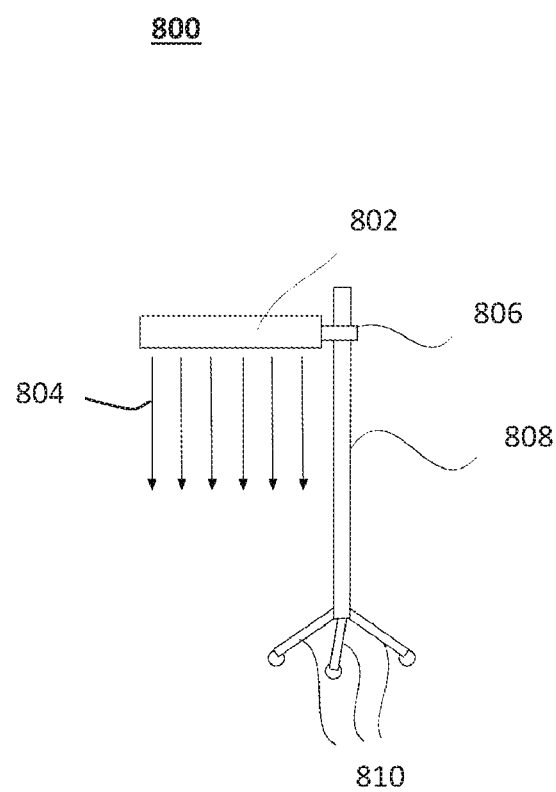
FIG. 8 is a side view of a vertically adjustable panel for inducing lipolysis, in accordance with some embodiments.

FIG. 8 shows an overhead panel device 800, in accordance with some embodiments. The overhead panel device 800 includes a height adjustable panel 802 that can include a plurality of LED emitters that emit light 804 onto a prone patient. The LED emitters can be configured or selected to emit light at various wavelengths as described herein. The panel 802 can be attached by an adjustable clamp 806 to a rolling stand 808 containing three legs 810 with caster wheels to allow mobility of the panel 802. The panel 802 can also contain one or more electromagnet coils (e.g. 28a, 28b) as previously described that are driven by a pulsed current generator according to a selected waveform. The panel 802 can be positioned over a patient who is lying prone and then adjusted to optimize the height over the patient. Bio-impedance sensors can be employed to monitor lipolysis and/or provide data to a microcontroller in the panel 802 to adjust, control, or modulate output from any combination of the systems (e.g. LED emitters, PEMF coils, etc.) that are present in the panel 802. The panel 802 can be sized to cover a portion of a patient, or it can be designed to be long enough to span the length of a patient while prone.

Figure 9:
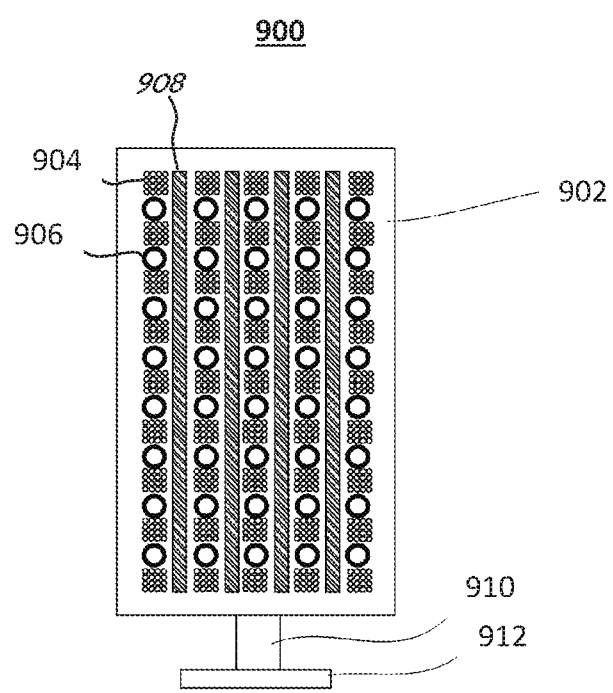
FIG. 9 is an elevational view of a stand-alone panel for inducing lipolysis, in accordance with some embodiments.

FIG. 9 shows a vertical panel device 900 for inducing lipolysis in a user, in accordance with some embodiments. The vertical panel device 900 can be used by a patient or user while the user is standing proximate to the panel device 900. The panel device 900 include a panel 902 that is mounted vertically to a stand 910 with base 912. The panel 902 is sized so that it will cover most a typical person's body in the vertical direction. In some embodiments the panel 902 can be on the order of about 18"-24" wide and 36"-48" high. The stand 910 can be height adjustable so as to allow positioning of the panel to correspond with the major portion of a user's body when standing next to the panel 902. In some embodiments the panel 902 can be equivalent to a wall of sauna device 8 of FIGS. 1-2.

The panel 902 can include a plurality of LED optical emitter groups 904 that emit selected wavelengths of light. In some embodiments the LED groups 904 can include a first plurality of LEDs configured to emit light of a first wavelength, and a second plurality of LEDs configured to emit light of a second wavelength. Additional LEDs for other wavelengths can be included as well. The LED groups are arranged in a matrix of rows and columns, but can be arranged equivalently in other arrangements, including being distributed uniformly across the surface of the panel 902.

The panel 902 can further include one or more electromagnetic coils 906 that are driven by a pulse generator. The coils 906 can be driven by a common generator, or individual or groups of coils can be driven by respective generators under control of a microprocessor in the panel 902. As with the LED groups 904, the coils 906 can be controlled in response to feedback received from one or more bio-sensors on and/or above the user's skin within sufficient proximity to measure conductance or conductance changes. Different bio-sensors can be assigned to, and applied to different parts of the user's body. Feedback from each bio-sensor can be used to control the LED groups 904, and coils 906 corresponding to the region of the user's body where the bio-sensors are located.

The panels 902 can further include one or more vents 908 through which temperature controlled air can be blown onto the user's body. The vents 908 can be columnar as shown, or arranged in any equivalent manner to provide temperature controlled airflow. The vents 908 can be substantially similar to vents 26 of FIG. 4, including fan units such as fan unit 600 of FIG. 6. The fan units can be controlled to a desired temperature to heat or cool the skin of the user, depending on the therapy regimen being applied, to facilitate lipolysis.

As discussed in reference to FIG. 1, two panels 902 can be used together, where the two panels 902 can be arranged adjacent each other and at ninety degrees to each other, forming a corner. The user can stand to face one panel 902 to allow that panel to act on the front of their body, while the adjacent panel acts on the side of the user's body. After a prescribed time, the user can then turn around and face the opposite direction to allow the user's back and other side to treated by the panels.

Figure 10:
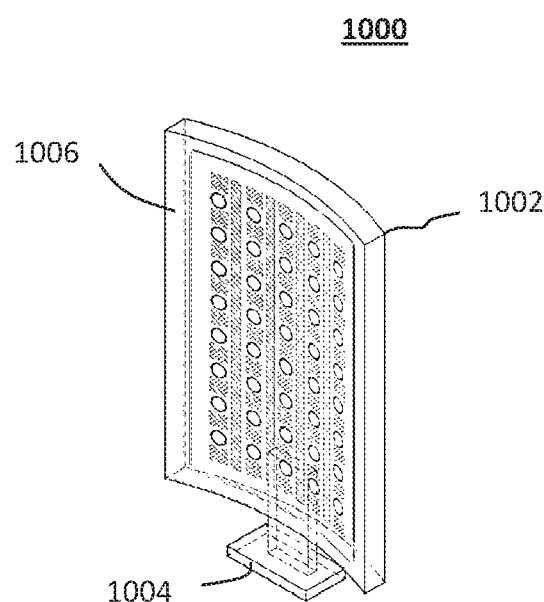
FIG. 10 is an elevational view of a stand-alone panel, having a curved surface, for inducing lipolysis, in accordance with some embodiments.

FIG. 10 is a perspective view of a curved panel device 1000 for inducing lipolysis, in accordance with some embodiments. The panel device 1000 includes a curved panel 1002 having a user-facing surface 1006 that is concave. The curved panel 1002 is mounted on a stand 1004 that can be height adjustable to raise or lower the curved panel 1002. The curved panel 1002 can otherwise by substantially identical to that of panel 902, and include LED emitters, coils, and vents, or combinations thereof, as described in reference to FIG. 9. The curved panel can increase the efficacy of the light emitted from the LED groups, making more of the light from the LED groups along the left and right sides of the panels incident on the user's skin. Likewise, the curved panel 1002 orients the magnetic field produced by the coils more directly at the user.

Figure 11:
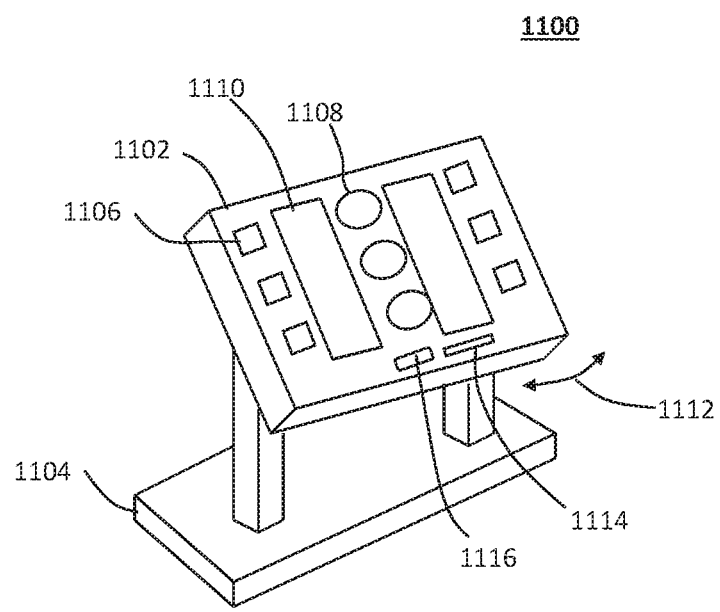
FIG. 11 is a perspective view of a desktop device for inducing lipolysis in a person's face and neck, in accordance with some embodiments.

FIG. 11 shows a perspective view of a desktop device 1100 for inducing lipolysis in a user, in accordance with some embodiments. The desktop device 1100 can be placed on a desk or table near a user and used to treat the face and neck of a user. The desktop device 1100 includes a panel 1102 that is mounted on a base 1104 or in an equivalent support structure. The panel 1102 can be mounted so as to have an adjustable tilt angle, as indicated by arrow 1112. The panel can comprise one or more LED groups 1104, one or more electromagnet coils 1108, and one or more vents 1110, which can all operate substantially as previously described. In particular, the LED groups can emit light in the 635 nm wavelength range, and in some embodiments can use LEDs emitting light in at both 635 nm and 850 nm wavelengths. The total light luminance can be between 20 mw/cm$^2$ and 500 mw/cm$^2$, and is directed towards the head, face, and neck. The modulation frequency of the LEDs can be performed using modulation frequencies between 0 Hz (continuous wave) and 2 GHz. In some embodiments the 635 nm LEDs will be driven by either a continuous current signal, or a signal that modulates at a frequency between 0.01 Hz and 40 KHz. In some embodiments the LEDs can be modulated at 80 Hz and/or at 300 Hz. In some embodiments the 635 nm LEDs can be modulated at 292 Hz, 584 Hz, 1,168 Hz, and 2,336 Hz. The modulation frequency of the 850 nm LEDs can be between 0 Hz (continuous wave) and 20,000 Hz. In some embodiments the modulation frequency of the 850 nm LEDs can be 40 Hz, 292 Hz, 584 Hz, 1,168 Hz, and/or 2,336 Hz. In some embodiments one or more of the coils 1108 can be configured for providing radio diathermy. A negative ion generator 1114 can be included as previously described, and a thermal camera 1116 can be used to receive thermal feedback based on an image of the user's face and neck during operation that can be used to control or select modulation operation of the LEDs, coils, and RF diathermy.

Figure 12:
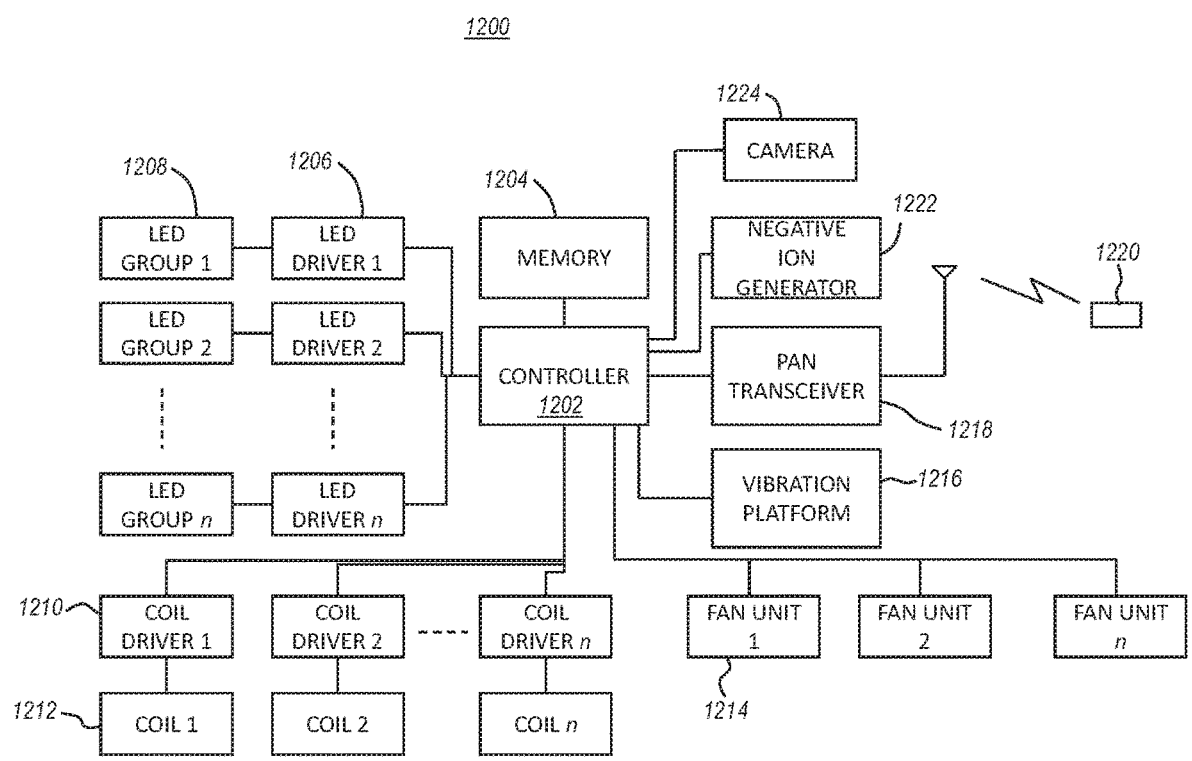
FIG. 12 is a block schematic diagram of a device for inducing lipolysis, in accordance with some embodiments.

FIG. 12 is a block schematic diagram of a lipolysis device 1200, in accordance with some embodiments. The lipolysis device 1200 can be incorporated into a sauna device, a panel, an overhead device, a desktop device, and so on, as described herein. The lipolysis device 1200 can be in each wall or panel of a multi-wall/panel configuration, such that there are a corresponding repetition of the device 1200, or the device 1200 can be configured to control all of the components on each one of the walls/panels of a multi-wall/panel configuration.

The device 1200 is operated by a controller 1202, which can be a microcontroller or microprocessor that performs instruction code that is designed to cause functionality of the various components of the device consistent with what has been described thus far in relation to the previous figures. The controller 1202 performs instruction code that is designed to cause the controller to carry out the desired control functionality by controlling and adjusting the output of certain components while receiving input from other components. The controller 1202 is coupled to a memory 1204 that represents an aggregate memory that can include various memory types such as read only memory (ROM), random access memory (RAM), flash memory, and other programmable memory. The memory can include the instruction code that is performed by the controller, and can also store variables and other operating data structures used during operation.

The controller 1202 can be coupled to one or more LED drivers 1206. The LED drivers are controllable power supplies that provide a controlled current to a respective group of LEDs 1208. The LED groups 1208 can each comprise LEDs that produce a selected wavelength of light. In some embodiments there can be several LED drivers 1206, as indicated numbering here of 1-n which each drive a corresponding LED group 1-n. In some embodiments different LED groups 1208 can comprise LEDs that produce different wavelengths of light. In some embodiments the LED groups 1208 can be arranged in a matrix of columns and rows of LED groups 1208, such as shown, for example, in FIGS. 3-4. In some embodiments each row can comprise LED groups that are configured to emit different wavelengths of light. Furthermore, the LED drivers 1206 can be controlled by the controller 1202 to modulate the light output of their respective LED groups 1208 according to a selected waveform. Thus, the controller 1202 can control the output of individual LED groups 1208 by a control signal provided by the controller 1202 to a respective LED driver 1206.

The controller 1202 is further configured to control the output of one or more electromagnetic coils 1212, numbered 1-n, by being coupled to a respective one or more coil drivers 1210 numbered 1-n. The coil drivers 1210 provide electric current to their respective coils 1212 to generate an electromagnetic field. The coils 1212 can be arranged such as shown, for example, in any of FIGS. 4, 7, and 9-11. In some embodiments only one coil 1212 and driver 1210 are used, as shown in FIG. 3, for example. Each of the coils 1212 (or coil when only one is present) can be driven to produce a time-varying magnetic field in correspondence with a selected waveform. In some embodiments each coil 1212 can be pulsed, meaning that they can be alternately energized and not energized to produce magnetic field pulses at a selected pulse frequency. In some embodiments the pulses, rather than being on/off, can be between a low output level and a high output level. In some embodiments when the coils 1212 are pulsed, a selected waveform can modulate the output of the coils 1212. In some embodiments, where multiple coils 1212 are present, different coils 1212 corresponding to different positions along a person's body can be controlled different, and specifically for that corresponding body portion. That is, different level of magnetic field output, as well as different pulse patterns and superimposed waveforms can be applied to different portions of the user's body. In some embodiments the coils 1212 can all have a uniform, non-varying magnetic field output.

The controller 1202 can be further coupled to one or more fan units 1214, numbered 1-n. The fan units 1214 can be substantially equivalent to that of FIG. 6, and can be used to control temperature inside a sauna unit, or to simply cool or warm the user's skin to enhance the effect of the light produced by the LED groups 1208 and the magnetic field output by the coil/coils 1212. In general, the fan units 1214 can be arranged to blow conditioned air through one or more vents that can have louvres for directing air flow as desired.

The controller 1202 can be further coupled to a vibration platform 1216 or similar vibration components that are used to impart vibration into the user's body tissue to aid in the lipolysis process. The vibration platform can be a component that the user stands or lays on in some embodiments. In some embodiments the vibration platform can be a component that emits ultrasonic acoustic waves in proximity to, or in contact with the user's body. The controller 1202 can control the vibration in frequency and amplitude according to a selected treatment regimen. In some embodiments the vibration platform can be pulsed (e.g. on/off, low/high) according to a selected treatment regimen.

The controller 1202 can be further coupled to a radio network transceiver, such as a personal area network (PAN) transceiver 1218. A personal area network uses very low power radio signals to communicate data according to a known air interface, such as those specified in the Institute for Electrical and Electronics Engineers (IEEE) specification 802.15. A commercial example of a PAN network transceiver is known by the tradename BLUETOOTH. The PAN transceiver 1218 can link with a bio-sensor 1220 using a defined radio air interface protocol so that the controller 1202 can receive sensed data from the bio-sensor that can be processed for feedback to control, for example, one or more LED groups 1208, one or more coils 1212, and/or the vibration platform 1216. The bio-sensor can measure skin conductance, and changes in skin conductance can indicate physiological changes in a user during treatment that can be used as feedback to adjust the treatment regimen during treatment. In some embodiments a sufficient change in skin conductance can indicate that the treatment regimen has reached a point where treatment is to be stopped, either as an identified end condition or for other reasons.

The controller can further be coupled to a camera unit 1224 that can include a three dimensional camera used to detect the position of various portions of the user's body relative to LED groups 1208 and coils 1212. In some embodiments the camera unit 1224 can include a thermal camera that is able to map and monitor a skin temperature of the user at various portions of the user's body. The position and/or temperature information can be used to adjust the output of the LED groups 1208 and/or the coils 1212, either together or individually based on location relative to the user's body. Various image processing and recognition algorithms are known that can be used by the controller 1202, or an associated image processor in the camera unit 1224 to recognize and determine the position of the portions of the user's body relative to portions of the lipolysis device 1200.

In some embodiments the controller 1202 can also control a negative ion generator 1222 to produce negative ions in the vicinity of the user during treatment and operation of the lipolysis device 1200. The negative ions can enhance the efficacy of topical substances applied prior to treatment.

The device 1200 is suitable for a variety of treatments in addition to lipolysis. For example, the electromagnetic coils can be used to generate electromagnetic fields that stimulate muscle contraction. By using suitably sized and spaced coils, specific muscles or muscle groups can be stimulated to contract momentarily. It is contemplated that video or equivalent image capture data can be analyzed using electromyography of athlete performing an exercise. This data can be used to generate a time sequence for muscle stimulation in general. The data can then be adapted to another individual using the camera 1224 to identify corresponding muscle locations on a specific user. The camera 1224 can be used to produce a three dimensional map of the user's body, and particular ones of the plurality of coils 1212 can be mapped to specific body portion locations, and then energized in a time sequence to simulate the exercise as performed by the athlete, originally. Both the camera 1224 and sensors 1220 can be used to provide anatomical measurements to the computer subsystem, such as height, leg length, chest size, etc. A training regimen can be created by the device by determining which coils 1212 need to be energized at a given time in the time sequence to replicate performance of the exercise in proper form.

When stimulated, the motor nerves innervating a muscle activate the same neurons in the brain and spine that fire during voluntary contraction at a decreased intensity. The nerves, spinal cord and brain can be "programmed" to perform exercises properly by being repeated exposed to the training regimen. The muscles will be programmed as well due to epigenetic changes that occur in response to repetitive muscle contraction. Examples of exercises that can be programmed this was can include, for example, a correct form to perform a squat, throw a baseball, etc. Additionally, novice athletes can acclimate to an exercise more rapidly by being exposed to a training regimen for a given exercise. When people with little to no exercise experience first begin exercising, the neuromuscular connection limits physical performance to a greater degree than intrinsic muscle strength. Using the training regimen for a given exercise can therefore speed up the rate at which a person can properly learn to perform a new exercise or movement. This can also be used in rehabilitation for patients that have lost certain brain function, such as stroke recovery patients, who have to "re-learn" movements and body control.

Figure 13:
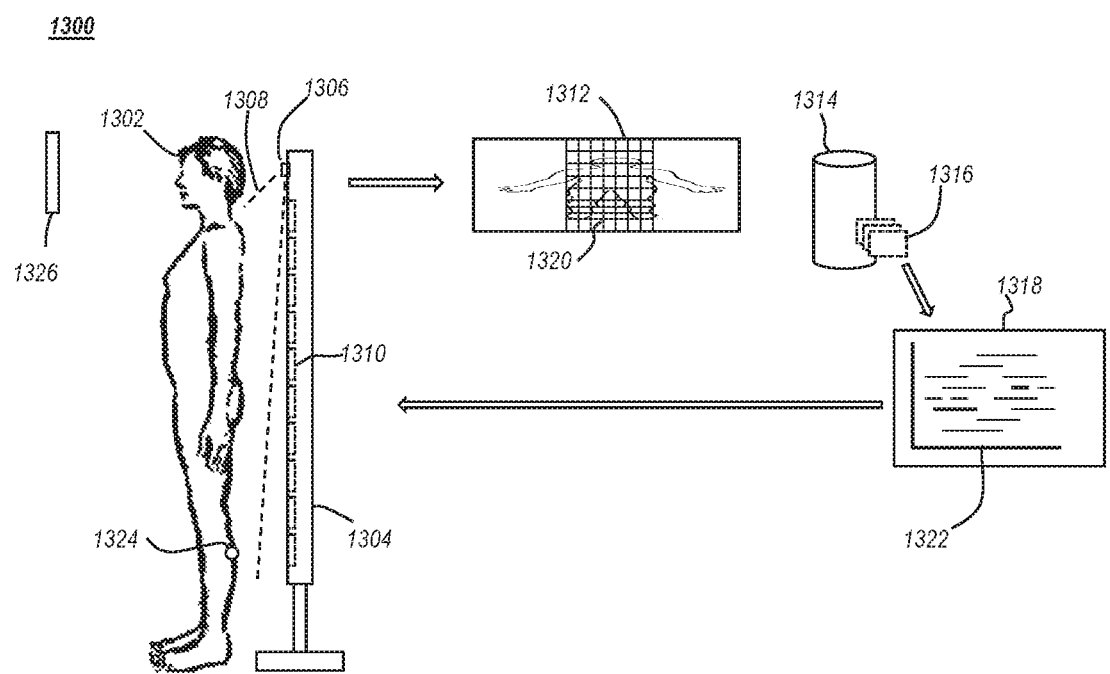
FIG. 13 is a process diagram of a method for inducing muscle stimulation according to a selected exercise, in accordance with some embodiments.

FIG. 13 is a process diagram of a process 1300 for inducing muscle stimulation according to a selected exercise, in accordance with some embodiments. A user 1302 can stand in front of a panel 1304 that contains a matrix of electromagnetic coils 1310 that can be energized at a selected frequency and output level (i.e. field strength magnitude) to apply PEMF to the user. The goal is to replicate specific muscle stimulation in a time synchronized manner to substantially replicate the performance of the exercise by an athlete. With the user 1302 standing in front of the panel 1304, a camera 1306 with a field of view 1308 is used to perform an image analysis of the user. Although shown here where the user 1302 has their back to the panel 1306, other panels can be provided to the sides of the user 1302 and in front of the user 1302 which are not shown here, but which will operate substantially similar to panel 1304.

The panel 1304 includes a processor and can be configured substantially as device 1200 of FIG. 12. In some embodiments panel 1304 may not include light emitting elements, using only electromagnetic coils 1304. The camera 1306 produces an image 1312 that can be analyzed and processed by the panel 1304 or at computing equipment connected to and controlling the panel 1304 to recognize portions of the body of the user 1302. In some embodiments, it is contemplated that coded stickers 1324 or appliques can be placed on corresponding body portions to make identifying their location in the image 1312 easier.

Once the image 1312 is processed to recognize body portions an overlay matrix 1320 can be applied to the image 1312. The overlay matrix is a matrix of rectangles in columns and rows where the height of the rectangles in each row decreases from top to bottom of the matrix 1320 to account for perspective. In some embodiments the camera 1306 can use two image capture systems, side by side, and image 1312 would then be a stereoscopic image which can aid in determining the position of body portions relative to the panel 1304. The body portions are then each mapped to the closest respective coil of the plurality of coils 1310; the mapped coil for each corresponding body portion will be energized to stimulate the muscle group in that body portion. Several body portions can be stimulated at the same time.

A database 1314 or other searchable data repository can be used to store the models 1316 of exercises performed by athletes. These models are produced by attaching electrodes to various body portions of the athlete and recording a representation of muscle activity when the athlete performs the exercise or movement. A video record of the athlete performing the exercise or movement can be used to identify the timing of muscle activity throughout the performance of the exercise or movement. This information is used to create a model 1316 of the exercise which maps muscle stimulation to time. The intensity and duration of muscle stimulation is recorded in the model as well.

A selected model 1316 can then be used to create an adapted model 1318 specifically for the body of the user 1302. In the adapted model 1318, the locations of specific coils are mapped to body portions to be stimulated to replicate the pattern of the athlete's performance of an exercise. In the adapted model 1322 the horizontal axis is time, increasing from left to right, and the vertical axis is mapped to coil locations in the panel 1304. As time commences, specific coils are energized at selected frequencies and intensities to stimulate the corresponding body portions of the user 1302. In some embodiments it is contemplated that, as the adapted model 1322 is "played" by the panel 1304, the user 1302 can watch a video of the performance of the exercise or movement that is synchronized to the playing of the adapted model 1322 such that the body portions of the user 1302 being stimulated are stimulated in time synchronization with that of the person in the video. The video can be played on a viewing device 1326 such as a monitor or headgear viewer.

Another use of the device (e.g. device 1200) uses resonant electromagnetic frequencies (rEMF) to simulate pharmaceuticals in order to affect the human body similarly to how the actual pharmaceutical would affect the body. The rEMFs that simulate morphine are effective in producing the analgesic effects of morphine without the physical drug. A known compound can be converted into electrical frequencies by obtaining its NMR spectrum, and then replicating the NMR spectrum though the electromagnetic coils (e.g. 1212) of the device. The NMR spectrum of most known compounds is readily available through online databases. If the spectrum is not known, it can be predicted with great accuracy using publicly available software. The rEMF required to simulate a given compound can be calculated from the NMR spectral shifts using the following formula:

$$rEMF = (\text{spectral shift (in ppm)}) \times (\text{The frequency of the NMR spectrometer}).$$

One rEMF will be found for each spectral shift for a given compound, a set of rEMFs can be calculated that has the same effect on the human body as a compound at a lower concentration. Alternatively, using predictive software known to those skilled in the art, a virtual "in silico" ligand having a desired structure can be created that can activate any receptor or molecular target in the human body. Additional software can translate the "in silico" ligand into an NMR spectrum. The NMR spectrum can then be translated into an rEMF set in the same manner as any existing compound. Alternatively, bioactive peptides can be designed using the Resonant Recognition Model (Cosic I, Pirogova E. Bioactive peptide design using the Resonant Recognition Model. Nonlinear Biomed Phys. 2007; 1(1):7. Published 2007 Jul. 19. doi:10.1186/1753-4631-1-7) and translated into rEMF after using software to predict the NMR spectrum of the bioactive peptide. This rEMF data set would then be an "in silicon" bioactive protein or peptide or a known DNA sequence. Once the rEMF for a compound "in silicon" ligand, or "in silicon" bioactive peptide is calculated, at least one of the rEMFs from the set can be applied to the body using the PEMF coils. One or more sets of rEMF may be applied to the body simultaneously, and different rEMF sets may be applied to different regions of the body. Alternatively, the rEMF set for a given compound or "in silicon" ligand may be divided among a plurality of coils with each coil emitting a portion of the rEMF set. The result is that the maximal pharmacological effect is produced at the intersection of the PEMF fields. Additionally, the LEDs and/or RF diathermy coils may be modulated at one or more rEMF frequencies. Lasers may be used to deliver the rEMF of botulinum toxin and/or the rEMF of an antibody against the nicotinic acetylcholine receptor on the postsynaptic membrane at the neuromuscular junction (such as Myasthenia Gravis Syndrome Antibodies) and/or antibodies against the presynaptic voltage-gated calcium channels in the neuromuscular junction (such as Lambert Eaton Syndrome Antibodies) to decrease wrinkles in the forehead via the photoelectric effect. A topical lotion may or may not be applied simultaneously to the skin containing monoclonal Myasthenia Gravis Syndrome Antibodies and or engineered functional equivalents of monoclonal Myasthenia Gravis Antibodies and/or monoclonal Lambert Eaton Syndrome Antibodies and/or engineered functional equivalents of monoclonal Lambert Eaton Syndrome Antibodies to provide a synergistic effect. Alternatively, an subdermal injection containing said antibodies may or may not be employed alone or additionally for synergistic effects and/or at least partial muscle paralysis. One or more sources of electromagnetic energy including PEMF, LEDs, and RF coils may be employed in addition to, or instead of lasers to deliver at least one frequency contained within the rEMF sets. At least one rEMF characteristic of one or more Jak-Stat inhibitor and/or minoxidil, and/or finasteride and/or B vitamins and/or epigallocatechin-3-gallate (EGCG) and/or NAD+, and/or ketoconazole and/or methylene blue and/or placenta extract and/or foreskin extract and/or platelet-rich plasma and/or trout sperm extract may be applied to the head to regrow hair and/or reverse graying; they may or may not be applied to other parts of the body to exert biological effects known to those skilled in the art of medicine. Other rEMF sets that may be employed include but are not limited to retinoids to reduce acne and wrinkles, antibiotics and antifungal agents to eliminate skin infections, agents known to enhance muscle growth, $\beta_2$ and $\beta_3$ agonists to enhance lipolysis, mitochondrial uncoupling agents that increase calorie expenditure, corticosteroids and NSAIDs to reduce inflammation, hydroquinone to even skin tone, cyclosporine to treat alopecia areata, alopecia totalis, and alopecia universalis, tofacitinib to treat psoriasis and arthritis, and human growth factors derived from cell cultures to regenerate cartilage and treat alopecia. The uses listed for each rEMF are demonstrative only, and do not represent the only biological use for those frequencies. The may or may not be applied to other regions of the body. The rEMF derived from any compound and/or "in silico" ligand and/or "in silico" bioactive peptide and/or combination of at least one frequency within a plurality of rEMF sets that treats disease in biological organisms and preferably the human body, effects cellular rejuvenation, affects respiration or redox reactions, assists in weight loss, increases muscle tone or fitness, results in slowing the aging process, increases lifespan, and/or increases the aesthetic value of the human physique may be employed by one or more of the PEMF, RF, LED and vibroacoustic subsystems. The health effects of the rEMF sets, lipolysis treatments and skin tightening may be monitored by in-vivo IR spectroscopy using commercially available sensors or devices such as that sold under the name "SCiO" (sold by Consumer Physics) mounted in the treatment chair or device (panel). The SCiO device can identify any compound in its database and could be used to measure common health indicators including but not limited to cholesterol, triglycerides, blood glucose levels, and cortisol levels. In vivo IR spectrometry may be employed in any embodiment of the device, irrespective of the use of rEMF fields.

In some embodiments, other spectra specific to the compound may be employed, including but not limited to infrared spectroscopy and/or its harmonic overtones and/or its harmonic undertones. Additionally, the harmonics of the NMR spectra and/or subharmonics of the NMR spectra may optionally be employed. In some embodiments, the rEMF signals may be embedded on a low carrier wave. This carrier wave may be the resonant frequency of the entire human body, a specific organ, a specific tissue type including but not limited to skin, bone, muscle, and fascia, or a specific cell type. Alternatively, the carrier wave may be in the kHz or GHz range in order to increase the energy and localization of the signal. Alternatively, the spectra and/or harmonics and/or subharmonics may be encoded onto electromagnetic radiation from low frequency EMF up to x-rays and gamma waves by passing them through an electromagnetic coil resonating at one or more rEMF fields. Alternatively, streams of ionized particles may pass through the electromagnetic coil and imprinted with the signature of the rEMF. In some embodiments, the plurality of coils may produce an electromagnetic hologram using the same mathematical transforms used to calculate optical and acoustic holograms. The electromagnetic hologram can produce one or more rEMF sets on a carrier wave preferably in the kHz to GHz range. The electromagnetic hologram may be static or vary with time. In some embodiments, the rEMF sets are produced by interference waves from at least two coils. In a two-coil system, each rEMF would be produced when one coil emits a fundamental frequency, and the second coil emits a frequency equal to the fundamental frequency+the rEMF. The fundamental frequency would preferably be in the kHz to Ghz range.

Figure 14:
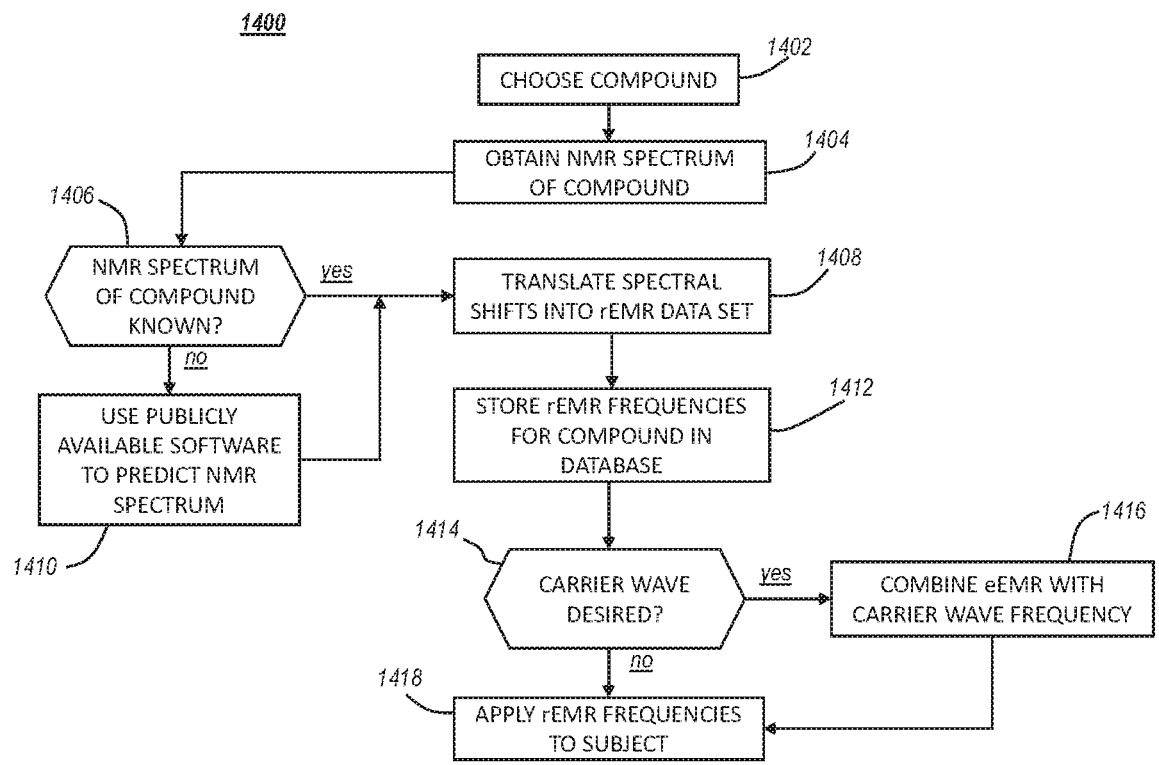
FIG. 14 is a flow chart diagram of a method for selecting and applying an rEMR to simulate the effect of a drug in a user, in accordance with some embodiments.

FIG. 14 is a flow chart diagram of a method 1400 for selecting and applying an rEMF to simulate the effect of a drug in a user, in accordance with some embodiments. In step 1402 a compound (pharmaceutical) is selected that is to be simulated. In step 1404 a process is commenced to obtain the nuclear magnetic resonance (NMR) of the compound. In step 1406 a first part of the process is determining whether the NMR of the compound is known. If it is, the method 1400 proceeds to step 1408. Otherwise, in step 1410, the NMR of the compound can be predicted using, for example, a software tool. In step 1408 the spectral shifts of the NMR for the selected compound are translated into a rEMF data set. The rEMF data set is used by the device (e.g. device 1200) to drive the various electromagnetic coils at appropriate frequencies to recreate the frequency spectrum of the NMR for the selected compound. In step 1412 the rEMF frequency list can be stored in, for example, a database. In step 1414 it is determined if a base carrier wave is desired. If so, then in step 1416 the base carrier wave frequency is combined with the rEMF frequencies. In step 1418 the rEMF frequencies are applied to the person receiving the treatment by selectively energizing coils at frequencies that interfere with each other to create the desired effect in the person receiving the treatment.

Figure 15:
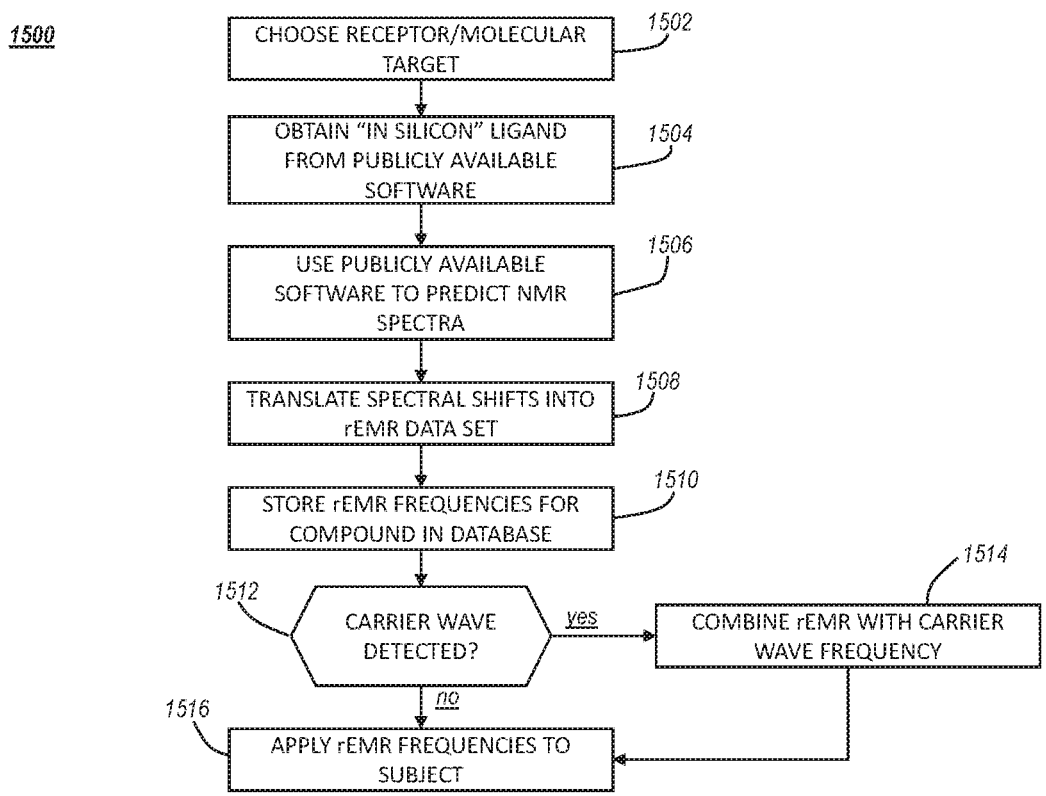
FIG. 15 is a flow diagram of a method for selecting and applying an rEMR to simulate the effect of a drug in a user, in accordance with some embodiments.

FIG. 15 is a flow diagram of a method 1500 for selecting and applying an rEMR to simulate the effect of a drug in a user, in accordance with some embodiments. method 1500 is similar to method 1400, but uses the "in silicon" ligand rather than the NMR of a substance. Accordingly, at step 1502 a particular compound is selected whose bio-active effect is to be simulated in a person. In step 1504 a process is commenced to obtain the "in silicon" ligand of the compound, which can be performed using, for example, known software tools in step 1506. In step 1508 the spectral shifts for the "in silicon" ligand are translated into an rEMF data set for the particular device (e.g. device 1200) being used. In step 1510 the rEMF frequencies can be stored for later use. IN step 1512 it is determined if a base carrier wave is desired. If so, then in step 1514 the base carrier wave frequency is combined with the rEMF frequencies. In step 1516 the EMF frequencies are applied to the person receiving the treatment by selectively energizing coils at frequencies that interfere with each other to create the desired effect in the person receiving the treatment.

For both methods 1400, 1500 the rEMF for acetylcholine (and/or other nicotinic cholinergic receptor agonists) and/or $Ca^{2+}$ and/or a vitamin D derivative (including, but not limited to 25-hydroxyvitamin D3) can be directed at the neuromuscular junction where EMF muscle contraction is employed in order to decrease the intensity of the magnetic field required. A MHz or GHz range carrier frequency may be employed to increase focus and penetration. The rEMF signatures of morphine may be applied to the spine or central nervous system to decrease the pain of magnetic muscle stimulation during treatment. The rEMF of thyroxine signatures can be directed into fat cells with or without a carrier signal in order to significantly increase lipolysis without dysregulating the thyroid and hypothalamic pituitary axis.

Contact free EEG sensors or sensors placed in light protection goggles worn by the user can be used to determine if a user is experiencing pain. The device (e.g. device 1200) could then decrease the temperature of diathermy, intensity of muscle contraction, etc. Recent studies indicate mood can be determined from EEG patterns: the data could be used to adjust machine parameters. These adjustments could be recorded for the particular patient and applied to future treatments. Only basic emotions such as pleasure, pain, anger, etc. are typically recognized. Alternatively, the cameras (e.g. camera 1224) can monitor heart rate variability and pulse, which are indicators of internal emotional state, and then treatment can be adjusted.

Figure 16:
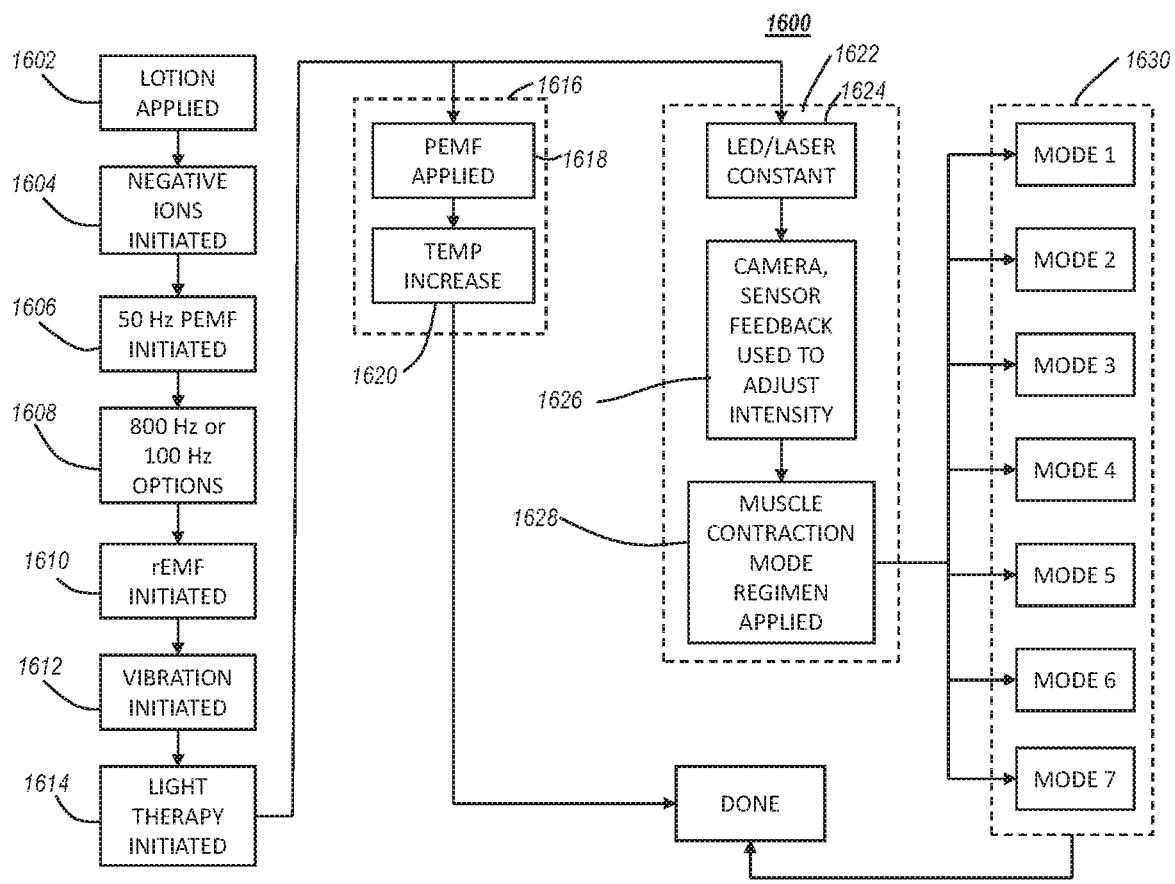
FIG. 16 is a flow chart diagram of a method for operating a device according to a desired regimen, in accordance with some embodiments.

FIG. 16 is a flow chart diagram of a method 1600 for operating a device according to a desired regimen, in accordance with some embodiments. The method 1600 shows a lipolysis treatment that can be performed alone, or in combination with a muscle stimulation treatment. Both treatments can begin with a common process or pre-process. For example, in step 1602 a selected topical substance (lotion, balm) can be applied to the skin of the person undergoing treatment. The topical substance can be any one of those listed hereinabove, and can be applied thirty to sixty minutes before commencing further treatment. In step 1604, the person undergoing treatment can position themselves adjacent a device such as a sauna device of FIGS. 1-2, a vertical panel, a desktop device, and overhead panel, a bed, or any other arrangement consistent with the teachings herein. IN some embodiments where the device includes a negative ion generator, in step 1604 negative ion generation can be initiated to expose the person undergoing treatment to negative ions, which can continue throughout the treatment. In step 1606 the coil or coils can be energized to create time varying PEMF electromagnetic field of about 50 Hertz which can remain ongoing throughout the treatment. In step 1608, which can be optionally applied, an 800 Hz PEMF field and/or a 100 Hz PEMF field can also be generated by the coil(s). An 800 Hz PEMF is the resonant frequency of cytochrome c oxidase and increases cellular transpiration, similar to that achieved with light therapy. A 100 Hz PEMF stimulates myoblast activity in skeletal muscle. In step 1610 selected rEMF treatment can be initiated where the rEMF frequencies can be selected to cause an effect in the person undergoing treatment to experience similar to that of a pharmaceutical, and other rEMF frequencies can be selected based on body composition as determined by image recognition, bio-impedance sensors, in vivo mass spectrometry, and gender. The rEMF, unlike PEMF, is constant and not pulsed, and uses different frequencies. The rEMF can continue throughout the treatment. In step 1612 a vibration treatment can be applied. In some embodiments a vibration platform can be used to provide mechanical vibrations that propagate through the person's body to facilitate lymphatic drainage. The frequency of the vibration can vary to target different portions of the body. In step 1614 light therapy can be applied. The light is generated by the plurality of LED light emitting components to induce lipolysis. The operator of the device can adjust the output of the various components to target specific areas of the body and to accomplish specific treatments. In some embodiments the device can make an assessment of the person using bio-impedance sensors and image recognition, and recommend a treatment regimen.

Steps 1602-1614 represent an initial process of the method 1600. The initial process can be continued alone for lipolysis, but in some embodiments further treatment modalities can be applied to treat musculature. Several examples are shown here, and include a brief treatment represented by the steps in box 1616, and a longer treatment including the steps in box 1622 and one or more of the modes of box 1630. For the brief treatment of box 1616, the goal is to increase intracellular ATP. This is achieved in step 1618 by specific, additional PEMF therapy or modulation of the PEMF being applied from steps 1606, 1608. In addition, in step 1620, the temperature control system can be used to adjust the temperature of the person's skin, and in particular, to increase the temperature. Temperature control can be accomplished by fan units (e.g. 600) that can warm or cool air being blown from the device. The treatments of steps 1618, 1620 can be applied for a brief period of time such as about five minutes.

In some embodiments the treatment can include a substantial muscle stimulation regimen, including, for example, simulated exercises or movements. When such treatment is desired, then the processes and steps of boxes 1622 and 1630 are followed from step 1614 (or any of the steps in 1602-1614). In step 1624 the light therapy provided by the plurality of LED optical emitters and/or lasers is initiated at a selected wavelength as previously discussed herein, and the light output can remain constant (rather than pulsed), but the wavelength can be varied or changed during treatment based on the person's Fitzpatrick skin scale category. That is a different light regimen can be selected and applied based on the person's skin type, as categorized under the Fitzpatrick skin scale in order to avoid damaging the skin. In step 1626 feedback from the camera and/or bio-impedance sensors can be initiated and used to monitor the person's skin exposure, temperature, impedance, and so on, and adjust the output intensity of the light therapy, and/or the PEMF intensity.

In step 1628 one of several modes of muscle contraction regimens are initiated, as selected by the person (or a treatment provider), and the method 1600 moves to box 1630 when one of several modes is followed. Each mode, shown here as modes 1-7, involves a different muscle stimulation regimen while the lipolysis inducing therapy is also applied. In each mode PEMF is used to cause muscular contraction at a selected body portion. The device can use a process such as that described in relation to FIG. 13. Each of modes 1-6 have a first sub-mode in which general stimulation is induced, and a second, alternative sub-mode where a timed stimulation pattern is induced to simulate performance of an exercise or movement.

In exemplary mode 1 there can be several sub-modes. In a first sub-mode, selected muscle groups are stimulated to contract periodically using PEMF to simulate endurance training. The contractions can be repeated as desired, and different muscle groups can be stimulated. This sub-mode is non-specific, and selectable by the person. In a second sub-mode, a particular exercise or movement is simulation by causing specific muscles to contract in a time synchronized manner as discussed in reference to FIG. 13 in order to simulate a particular exercise or movement as performed by, for example, an expert such as a professional athlete or exercise instructor. The synchronized stimulation, in addition to exercising the muscles, conditions the person's muscle memory such that repeating the exercise or movement correctly is able to be accomplished much sooner than if the person simply tied repeating the exercise or movement without the externally induced stimulation.

In exemplary mode 2, a low repetition weight training regimen can be replicated to stimulate slow twitch muscles. Once the person is standing adjacent the device, the person's muscle locations relative to the PEMF coils can be mapped by the device, or by an operator of the device, and the appropriate slow twitch muscles can be stimulated. In first sub-mode of mode 2, simple muscular contractions are induced in targeted slow twitch muscle groups to promote muscular strength and hypertrophy. In a second sub-mode of mode 2, nerve stimulation with no or minimal muscular contraction is induced by the device according to a time synchronized stimulation pattern that replicates a weight lifting exercise.

Exemplary mode 3 is used to simulate high repetition weight training, and in particular, stimulating fast twitch muscles/muscle fibers. Again, a first sub-mode is used to generally stimulate the fast twitch muscles while a second sub-mode can be used to stimulate the fast twitch muscles according to a time synchronized pattern to replicate performance of an exercise or movement. Exemplary mode 4 is used to simulate the effect of mixed training, where a combination of fast and slow twitch muscles are stimulated, either according to the first sub-mode or the second sub-mode. Exemplary mode 5 can stimulate specific body regions without regard to muscle type, and more to achieve a desired body aesthetic. For example, the arms, buttocks, and abdomen can be stimulated. Both the first and second sub-modes can be applied. In exemplary mode 6 rehabilitation of injured or otherwise negatively affected muscles can be stimulated to regain muscle use, achieve symmetric muscle performance, to the extent possible, can be achieved, using either the first or second sub-modes.

In exemplary mode 7, PEMF is applied only to selected body areas not receiving muscle stimulation, in conjunction, alternating periods of localized RF diathermy and cooling cycles can be applied to tighten skin. RF diathermy adipocyte ablation will be active periodically for short lengths of time to allow cells to be shrunk by light therapy to be ablated rapidly. The frequency and length of ablative periods can be controlled using feedback data from image processing images of the person's body, as well as bio-impedance sensors, during treatment. A period of PEMF microcurrent induction can be used to increase cellular ATP, decrease discomfort experienced during the treatment, and accelerate muscle recovery and hypertrophy. After the light and PEMF treatment, the fan/vent system can be used to cool the person's body. Hydration and supplements of antioxidants, amino acids, protein, and structured water are beneficial in combination with this mode of treatment.

A device and method for inducing lipolysis has been disclosed that uses light and electromagnetic/magnetic fields to induce lipolysis in a human subject. The effect of these treatment modalities can be augmented by the use of selected topical treatments, as well as by the application of mechanical agitation of the subject's tissue through vibration. During treatment forms of feedback (e.g. skin conductance, thermo-visual) can be used to adjust the operation the treatment modalities to optimize their effect. As a result, the device and method are capable of inducing lipolysis in humans in a way that can rapidly facilitate the elimination of unwanted adipose fat, either at selected location on the body or for substantially the user's entire body in a way that has not been achieved previously.

What is claimed is:

1. A device for inducing lipolysis in a person, comprising:
   at least one wall having a front surface, the front surface being vertical;
   a plurality of light emitting elements disposed on the front surface of the wall that are configured to emit at least one selected wavelength of light;
   at least one electromagnetic coil disposed on the front surface of the wall and configured to project an electromagnetic field in a direction that is substantially perpendicular to the front surface;
   a vibration platform that is positioned at a bottom of the wall and which is configured for a person to stand on such that the plurality of light emitting elements and the at least one electromagnetic coil face toward the person when the person is standing on the vibration platform, the vibration platform is further configured to impart vibration into a body of the person while the person is being exposed to light from the plurality of light emitting elements and the electromagnetic field of the at least one electromagnetic coil; and
   a controller operatively coupled to the plurality of light emitting elements, the at least one electromagnetic coil, and vibration platform, wherein the controller is configured to control the plurality of light emitting elements, the at least one electromagnetic coil, and vibration platform according to a selected treatment regimen, and wherein at least a portion of the selected treatment regimen includes controlling the plurality of light emitting elements, the at least one electromagnetic coil, and vibration platform to act on the person simultaneously.

2. The device of claim 1, wherein the at least one wall is a plurality of walls that are configured to substantially surround the vibration platform on different sides of the vibration platform.

3. The device of claim 1, wherein the plurality of light emitting elements are a plurality of light emitting diode (LEDs).

4. The device of claim 3, the plurality of LEDs are arranged in a plurality of LED groups, and wherein the plurality of LED groups are arranged in a matrix of rows and columns.

5. The device of claim 1, wherein the at least one electromagnetic coil is configured around a border of the front surface of the at least one wall and surrounding the plurality of light emitting elements in the front surface of the wall.

6. The device of claim 1, wherein the at least one electromagnetic coil comprises a plurality of coils disposed on at least one wall.

7. The device of claim 1, wherein at least some of the plurality of light emitting elements are configured to emit light having a wavelength of one of 635 nm, 850 nm, or 980 nm.

8. The device of claim 1, wherein a first portion of the plurality of light emitting elements is configured to emit light at a first wavelength, and a second portion of the plurality of light emitting elements is configured to emit light at a second wavelength.

9. The device of claim 1, further comprising a negative ion generator that is controlled to be operable during a treatment regimen.

10. The device of claim 1, wherein the plurality of light emitting elements are controlled to output light according to a modulation waveform.

11. The device of claim 1, wherein the electromagnetic field of the at least one electromagnetic coil is pulsed.

12. The device of claim 11, wherein the electromagnetic field is produce having a frequency in the range of 0-100,000 Hertz.

13. The device of claim 1, wherein the light emitted by the plurality of light emitting elements and the electromagnetic field produced by the at least one electromagnetic coil are adjusted during a treatment regimen based on feedback received by the controller from a sensor device that is configured to sense at least one of a position of: the person relative to the at least one wall, or a biological condition of the person.

14. The device of claim 13, wherein the sensor device is a camera having a field of view, wherein the camera produces images of the person in the field of view, and wherein the feedback comprises differences in successive images of the person during the treatment regimen.

15. The device of claim 13, wherein the device further comprises a network radio transceiver, wherein the network radio transceiver is configured to receive signals from a bio-impedance sensor placed on the body of the person, and wherein the feedback comprises changes in bio-impedance in the body of the person over time.

16. A light sauna for inducing lipolysis in a person, comprising:
   at least two panels arranged vertically and perpendicular to each other, with a vertical edge of a first one of the at least two panels proximate to a vertical edge of a second one of the at least two panels thereby forming a corner, each of the at least two panels forming a wall of the light sauna and having an inward-facing surface at an interior of the light sauna;

each of the at least two panels having:
- a plurality of light emitting elements disposed on the inward-facing surface of the panel that are configured to emit at least one selected wavelength of light;
- at least one electromagnetic coil configured to project an electromagnetic field in a direction that is substantially perpendicular to the inward-facing surface; and
- a vibration platform positioned at a bottom of each of the at least two panels at the interior of the light sauna, the vibration platform configured to provide vibration to a person while the person is standing on the vibration platform and while light is emitted from the plurality of light emitting elements and while the electromagnetic field is being projected.

17. The light sauna of claim 16, wherein the at least one electromagnetic coil is a coil that surrounds the plurality of light elements on the panel.

18. The light sauna of claim 16, wherein each one of the at least two panels further comprises at least one vent and a chilling unit configured to blow chilled air into the interior of the light sauna.

19. The light sauna of claim 16, wherein a first portion of the plurality of light emitting elements is configured to emit light at a first wavelength, and a second portion of the plurality of light emitting elements is configured to emit light at a second wavelength.

20. the light sauna of claim 16, wherein the at least two panels comprises four panel arranged to surround the vibration platform, and wherein one of the four panels comprises a door.

* * * * *